(12) United States Patent
Klein et al.

(10) Patent No.: US 6,942,995 B2
(45) Date of Patent: *Sep. 13, 2005

(54) METHODS OF CREATING CONSTRUCTS USEFUL FOR INTRODUCING SEQUENCES INTO EMBRYONIC STEM CELLS

(75) Inventors: Robert D. Klein, Palo Alto, CA (US); Thomas J. Brennan, South San Francisco, CA (US)

(73) Assignee: Deltagen, Inc., San Carlos, CA (US)

( * ) Notice: Subject to any disclaimer, the term of this patent is extended or adjusted under 35 U.S.C. 154(b) by 393 days.

This patent is subject to a terminal disclaimer.

(21) Appl. No.: 10/087,523

(22) Filed: Feb. 28, 2002

(65) Prior Publication Data

US 2002/0197624 A1 Dec. 26, 2002

Related U.S. Application Data

(63) Continuation of application No. 09/193,834, filed on Nov. 17, 1998, now abandoned.
(60) Provisional application No. 60/084,949, filed on May 11, 1998, and provisional application No. 60/084,194, filed on Nov. 17, 1997.

(51) Int. Cl.$^7$ .................. C12N 15/64; C12N 15/00; C12P 19/34; C12Q 1/68; C07H 21/04
(52) U.S. Cl. .................. 435/91.4; 435/91.1; 435/91.2; 435/91.5; 435/320.1; 435/6; 536/23.1
(58) Field of Search .................. 435/91.1, 91.4, 435/320.1, 6; 536/23.1

(56) References Cited

U.S. PATENT DOCUMENTS

| | | | |
|---|---|---|---|
| 5,137,814 A | 8/1992 | Rashtchian et al. | |
| 5,464,764 A | 11/1995 | Capecchi et al. | |
| 5,487,992 A | 1/1996 | Capecchi et al. | |
| 5,627,059 A | 5/1997 | Capecchi et al. | |
| 5,631,153 A | 5/1997 | Capecchi et al. | |
| 5,714,667 A | 2/1998 | Waterhouse et al. | |
| 6,815,185 B2 * | 11/2004 | Klein et al. | 435/91.4 |

FOREIGN PATENT DOCUMENTS

| | | |
|---|---|---|
| WO | WO 93/18175 | 9/1993 |
| WO | WO 94/06908 | 3/1994 |

OTHER PUBLICATIONS

Aslanidis et al., 1990, Nucletic Acids Res., 18(20): 6069–6074, "Ligation–independent cloning of PCR products (LIC–PCR)."

Gubin et al., 1997, Biochem. Biophys. Res. Comm., 236: 347–350, "Long–Term, Stable Expression of Green Fluorescent Protein in Mammalian Cells."

Randolph et al., 1996, Transgenic REs., 5(6): 413–420, "PCR–based Gene Targeting of the Inducible Nitric Oxide Synthase (NOS2) Locus in Murine ES Cells, a New and More Cost–effective Approach."

Rizzuto et al., 1995, Current Biology, 5: 635–642, "Chimeric green fluorescent protein as a tool for visualizing subcellular organelles in living cells."

Stratagene et al., Stratagene Catalog, 1997–1998, p35, "PCR Cloning and Plasmid Construction."

(Continued)

Primary Examiner—Gerry Leffers
(74) Attorney, Agent, or Firm—John E. Burke; Greenberg Traurig LLP

(57) ABSTRACT

This invention provides novel nucleotide constructs. Also provided are methods for making DNA constructs useful for introducing sequences into and disrupting the function of a gene in a cell, particularly an embryonic stem cell.

15 Claims, 11 Drawing Sheets

OTHER PUBLICATIONS

Karaplis et al., Methods in Bone Research: 1189–1201, "Gene Targeting."

US Dept. Health & Human Service, 1992, "Modified Vectors for ligation–independent cloning–using extended single–stranded complimentary tails on vectors and a foreign protein encoding sequence."

Aslanidis et al., 1994, PCR Methods and Applications, 4: 172–177, "Minimal Length Requirement of the Single–stranded Tails for Ligation–independent Cloning of PCR Products."

Ausubel F.M. et al., 1995, Current Protocols in Molecular Bio., (Table of Contents).

Freshney, R.I., Ed., 1987, IRL Press, "Animal Cell Culture: a practical approach."

Jakoby, W.B., et al. Eds., 1979, Methods in Enzymology, vol. LVIII Cell Culture, Academic Press, Inc. (Table of Contents).

McPherson, M.J. et al., 1995, IRL Press, PCR 2: A Practical Approach (Table of Contents).

Munroe et al., 1995, Proc. Nat'l Acad. Sci., USSA 92(6): 2209–2213, "Systematic Screening of an Arrayed cDNA Library by PCR."

Rashtchian, 1995, Current Opinion in Biotech., 6: 30–36, "Novel Methods for Cloning and Engineering Genes Using the Polymerase Chain Reaction."

Sambrook et al., 1989, Molecular Cloning: A Laboratory Manual, 2nd Ed., Cold Spring Harbor Lab. Press (Table of Contents).

Sampath et al., 1997, Gene 190: 5–10 "Versatile Vectors for Direct Cloning and Ligation–independent cloning of PCR–amplified fragments for surface display on filamentous bacteriophages."

Yu et al., 1996, Methods Mol. Bio. 58: 335–339, "Use of Polymerase Chain Reaction to Screen Phage Libraries."

* cited by examiner

```
GTTAACTACG TCAGGTGGCA CTTTTCGGGG AAATGTGCGC GGAACCCCTA TTTGTTTATT TTTCTAAATA CATTCAAATA
TGTATCCGCT CATGAGACAA TAACCCTGAT AAATGCTTCA ATAATATTGA AAAAGGAAGA GTATGAGTAT TCAACATTTC
CGTGTCGCCC TTATTCCCTT TTTTGCGGCA TTTTGCCTTC CTGTTTTTGC TCACCCAGAA ACGCTGGTGA AAGTAAAAGA
TGCTGAAGAT CAGTTGGGTC CACGAGTGGG TTACATCGAA CTGGATCTCA ACAGCGGTAA GATCCTTGAG AGTTTTCGCC
CCGAAGAACG TTCTCCAATG ATGAGCACTT TTAAAGTTCT GCTATGTGGC GCGGTATTAT CCCGTGTTGA CGCCGGGCAA
GAGCAACTCG GTCGCCGCAT ACACTATTCT CAGAATGACT TGGTTGAGTA CTCACCAGTC ACAGAAAAGC ATCTTACGGA
TGGCATGACA GTAAGAGAAT TATGCAGTGC TGCCATAACC ATGAGTGATA ACACTGCGGC CAACTTACTT CTGACAACGA
TCGGAGGACC GAAGGAGCTA ACCGCTTTTT TGCACAACAT GGGGGATCAT GTAACTCGCC TTGATCGTTG GGAACCGGAG
CTGAATGAAG CCATACCAAA CGACGAGCGT GACACCACGA TGCCTGTAGC AATGGCAACA ACGTTGCGCA AACTATTAAC
TGGCGAACTA CTTACTCTAG CTTCCCGGCA ACAATTAATA GACTGGATGG AGGCGGATAA AGTTGCAGGA CCACTTCTGC
GCTCGGCCCT TCCGGCTGGC TGGTTTATTG CTGATAAATC TGGAGCCGGT GAGCGTGGGT CTCGCGGTAT CATTGCAGCA
CTGGGGCCAG ATGGTAAGCC CTCCCGTATC GTAGTTATCT ACACGACGGG GAGTCAGGCA ACTATGGATG AACGAAATAG
ACAGATCGCT GAGATAGGTG CCTCACTGAT TAAGCATTGG TAACTGTCAG ACCAAGTTTA CTCATATATA CTTTAGATTG
ATTTACCCCG GTTGATAATC AGAAAAGCCC CAAAAACAGG AAGATTGTAT AAGCAAATAT TTAAATTGTA AACGTTAATA
TTTTGTTAAA ATTCGCGTTA AATTTTTGTT AAATCAGCTC ATTTTTTAAC CAATAGGCCG AAATCGGCAA AATCCCTTAT
AAATCAAAAG AATAGCCCGA GATAGGGTTG AGTGTTGTTC CAGTTTGGAA CAAGAGTCCA CTATTAAAGA ACGTGGACTC
CAACGTCAAA GGGCGAAAAA CCGTCTATCA GGGCGATGGC CCACTACGTG AACCATCACC CAAATCAAGT TTTTTGGGGT
CGAGGTGCCG TAAAGCACTA AATCGGAACC CTAAAGGGAG CCCCCGATTT AGAGCTTGAC GGGGAAAGCG AACGTGGCGA
GAAAGGAAGC GAAGAAAGCG AAAGGAGCGG GCGCTAGGGC GCTGGCAAGT GTAGCGGTCA CGCTGCGCGT AACCACCACA
CCCGCCGCGC TTAATGCGCC GCTACAGGGC GCGTAAAAGG ATCTAGGTGA AGATCCTTTT TGATAATCTC ATGACCAAAA
TCCCTTAACG TGAGTTTTCG TTCCACTGAG CGTCAGACCC CGTAGAAAAG ATCAAAGGAT CTTCTTGAGA TCCTTTTTTT
CTGCGCGTAA TCTGCTGCTT GCAAACAAAA AAACCACCGC TACCAGCGGT GGTTTGTTTG CCGGATCAAG AGCTACCAAC
TCTTTTTCCG AAGGTAACTG GCTTCAGCAG AGCGCAGATA CCAAATACTG TTCTTCTAGT GTAGCCGTAG TTAGGCCACC
ACTTCAAGAA CTCTGTAGCA CCGCCTACAT ACCTCGCTCT GCTAATCCTG TTACCAGTGG CTGCTGCCAG TGGCGATAAG
TCGTGTCTTA CCGGGTTGGA CTCAAGACGA TAGTTACCGG ATAAGGCGCA GCGGTCGGGC TGAACGGGGG GTTCGTGCAC
ACAGCCCAGC TTGGAGCGAA CGACCTACAC CGAACTGAGA TACCTACAGC GTGAGCTATG AGAAAGCGCC ACGCTTCCCG
AAGGGAGAAA GGCGGACAGG TATCCGGTAA GCGGCAGGGT CGGAACAGGA GAGCGCACGA GGGAGCTTCC AGGGGGAAAC
GCCTGGTATC TTTATAGTCC TGTCGGGTTT CGCCACCTCT GACTTGAGCG TCGATTTTTG TGATGCTCGT CAGGGGGGCG
GAGCCTATGG AAAAACGCCA GCAACGCGGC CTTTTTACGG TTCCTGGCCT TTTGCTGGCC TTTTGCTCAC ATGTAATGTG
AGTTAGCTCA CTCATTAGGC ACCCCAGGCT TTACACTTTA TGCTTCCGGC TCGTATGTTG TGTGGAATTG TGAGCGGATA
ACAATTTCAC ACAGGAAACA GCTATGACCA TGATTACGCC AAGCTACGTA ATACGACTCA CTAGGCGGCC GCGTTTAAAC
AATGTGCTCC TCTTTGGCTT GCTTCCGCGG GCCAAGCCAG ACAAGAACCA GTTGACGTCA AGCTTCCCGG GACGCGTGCT
AGCGGCGCGC CGAATTCCTG CAGGATTCGA GGGCCCCTGC AGGTCAATTC TACCGGGTAG GGGAGGCGCT TTTCCCAAGG
CAGTCTGGAG CATGCGCTTT AGCAGCCCCG CTGGCACTTG GCGCTACACA AGTGGCCTCT GGCCTCGCAC ACATTCCACA
TCCACCGGTA GCGCCAACCG GCTCCGTTCT TTGGTGGCCC CTTCGCGCCA CCTTCTACTC CTCCCCTAGT CAGGAAGTTC
CCCCCCGCCC CGCAGCTCGC GTCGTGCAGG ACGTGACAAA TGGAAGTAGC ACGTCTCACT AGTCTCGTGC AGATGGACAG
CACCGCTGAG CAATGGAAGC GGGTAGGCCT TTGGGGCAGC GGCCAATAGC AGCTTTGCTC CTTCGCTTTC TGGGCTCAGA
GGCTGGGAAG GGGTGGGTCC GGGGCGGGC TCAGGGCGG GCTCAGGGGC GGGGCGGGCG CGAAGGTCCT CCGAGGCCC
GGCATTCTCG CACGCTTCAA AAGCGCACGT CTGCCGCGCT GTTCTCCTCT TCCTCATCTC CGGGCCTTTC GACCTGCAGC
CAATATGGGA TCGCCATTG AACAAGATGG ATTGCACGCA GGTTCTCCGG CCGCTTGGGT GGAGAGGCTA TTCGGCTATG
ACTGGGCACA ACAGACAATC GGCTGCTCTG ATGCCGCCGT GTTCCGGCTG TCAGCGCAGG GGCGCCCGGT TCTTTTTGTC
AAGACCGACC TGTCCGGTGC CCTGAATGAA CTGCAGGACG AGGCAGCGCG GCTATCGTGG CTGGCCACGA CGGGCGTTCC
TTGCGCAGCT GTGCTCGACG TTGTCACTGA AGCGGGAAGG GACTGGCTGC TATTGGGCGA AGTGCCGGGG CAGGATCTCC
TGTCATCTCA CCTTGCTCCT GCCGAGAAAG TATCCATCAT GGCTGATGCA ATGCGGCGGC TGCATACGCT TGATCCGGCT
ACCTGCCCAT TCGACCACCA AGCGAAACAT CGCATCGAGC GAGCACGTAC TCGGATGAA GCCGGTCTTG TCGATCAGGA
TGATCTGGAC GAAGAGCATC AGGGGCTCGC GCCAGCCGAA CTGTTCGCCA GGCTCAAGGC GCGCATGCCC GACGGCGATG
ATCTCGTCGT GACCCATGGC GATGCCTGCT TGCCGAATAT CATGGTGGAA AATGGCCGCT TTTCTGGATT CATCGACTGT
GGCCGGCTGG GTGTGGCGGA CCGCTATCAG GACATAGCGT TGGCTACCCG TGATATTGCT GAAGAGCTTG GCGGCGAATG
GGCTGACCGC TTCCTCGTGC TTTACGGTAT CGCCGCTCCC GATTCGCAGC GCATCGCCTT CTATCGCCTT CTTGACGAGT
TCTTCTGAGG GGATCGATCC GTCCTGTAAG TCTGCAGAAA TTGATGATCT ATTAAACAAT AAAGATGTCC ACTAAAATGG
AAGTTTTTCC TGTCATACTT TGTTAAGAAG GGTGAGAACA GAGTACCTAC ATTTTGAATG GAAGGATTGG AGCTACGGGG
GTGGGGGTGG GGTGGGATTA GATAAATGCC TGCTCTTTAC TGAAGGCTCT TTACTATTGC TTTATGATAA TGTTTCATAG
TTGGATATCA TAATTTAAAC AAGCAAAACC AAATTAAGGG CCAGCTCATT CCTCCCACTC ATGATCTATA GATCTATAGA
TCTCTCGTGG GATCATTGTT TTTCTCTTGA TTCCCACTTT GTGGTTCTAA GTACTGTGGT TTCCAAATGT GTCAGTTTCA
TAGCCTGAAG AACGAGATCA GCAGCCTCTG TTCCACATAC ACTTCATTCT CAGTATTGTT TTGCCAAGTT CTAATTCCAT
CAGAAGCTGA CTCTAGATCT GGATCCGGCC AGCTAGGCCG TCGACCTCGA GTGATCAGGT ACCAAGCTGC TCGCTCTGTG
TCCGTTGAGC TCGACGACAC AGGACACGCA AATTAATTAA GGCCGGCCCG TACCCTCTAG TCAAGGCCTT AAGTGAGTCG
TATTACCGAC TGGCCGTCGT TTTACAACGT CGTGACTGGG AAAACCCTGG CGTTACCCAA CTTAATCGCC TTGCAGCACA
TCCCCCTTTC GCCAGCTGGC GTAATAGCGA AGAGGCCCGC ACCGATCGCC CTTCCCAACA GTTGCGCAGC CTGAATGGCG
AATGGCGCTT CGCTTGGTAA TAAAGCCCGC TTCGGCGGGC TTTTTTTT
```

FIGURE 2B

```
GTTTAATAGT AATCAATTAC GGGGTCATTA GTTCATAGCC CATATATGGA GTTCCGCGTT ACATAACTTA CGGTAAATGG
CCCGCCTGGC TGACCGCCCA ACGACCCCCG CCCATTGACG TCAATAATGA CGTATGTTCC CATAGTAACG CCAATAGGGA
CTTTCCAATG ACGTCAATGG GTGGAGTATT TACGGTAAAC TGCCCACTTG GCAGTACATC AAGTGTATCA TATGCCAAGT
ACGCCCCCTA TTGACGTCAA TGACGGAAAA TGGCCCGCCT GGCATTAAGC CCAGTACATG ACCTTATGGG ACTTTCCTAC
TTGGCAGTAC ATCTACGTAT TAGTCATCGC TATTACCATG GTGATGCGGT TTTGGCAGTA CATCAATGGG CGTGGATAGC
GGTTTGACTC ACGGGGATTT CCAAGTCTCC ACCCCATTGA CGTCAATGGG AGTTTGTTTT GGCACCAAAA TCAACGGGAC
TTTCCAAAAT GTCGTAACAA CTCCGCCCCA TTGACGCAAA TGGGCGGTAG GCGTGTACGG TGGGAGGTCT ATATAAGCAG
AGCTGGTTTA GTGAACCGTC AGATCCGCTA GCGCTACCGG TCGCCACCAT GGTGAGCAAG GGCGAGGAGC TGTTCACCGG
GGTGGTGCCC ATCCTGGTCG AGCTGGACGG CGACGTAAAC GGCCACAAGT TCAGCGTGTC CGGCGAGGGC GAGGGCGATG
CCACCTACGG CAAGCTGACC CTGAAGTTCA TCTGCACCAC CGGCAAGCTG CCCGTGCCCT GGCCCACCCT CGTGACCACC
CTGACCTACG GCGTGCAGTG CTTCAGCCGC TACCCCGACC ACATGAAGCA GCACGACTTC TTCAAGTCCG CCATGCCCGA
AGGCTACGTC CAGGAGCGCA CCATCTTCTT CAAGGACGAC GGCAACTACA AGACCCGCGC CGAGGTGAAG TTCGAGGGCG
ACACCCTGGT GAACCGCATC GAGCTGAAGG GCATCGACTT CAAGGAGGAC GGCAACATCC TGGGGCACAA GCTGGAGTAC
AACTACAACA GCCACAACGT CTATATCATG GCCGACAAGC AGAAGAACGG CATCAAGGTG AACTTCAAGA TCCGCCACAA
CATCGAGGAC GGCAGCGTGC AGCTCGCCGA CCACTACCAG CAGAACACCC CCATCGGCGA CGGCCCCGTG CTGCTGCCCG
ACAACCACTA CCTGAGGACC CAGTCCGCCC TGAGCAAAGA CCCCAACGAG AAGCGCGATC ACATGGTCCT GCTGGAGTTC
GTGACCGCCG CCGGGATCAC TCTCGGCATG GACGAGCTGT ACAAGTCCGG ACTCAGATCC ACCGGATCTA GATAACTGAT
CATAATCAGC CATACCACAT TTGTAGAGGT TTTACTTGCT TTAAAAAACC TCCCACACCT CCCCCTGAAC CTGAAACATA
AAATGAATGC AATTGTTGTT GTTAACTTGT TTATTGCAGC TTATAATGGT TACAAATAAA GCAATAGCAT CACAAATTTC
ACAAATAAAG CATTTTTTTC ACTGCATTCT AGTTGTGGTT TGTCCAAACT CATCAATGTA TCTTAACGCG AACTACGTCA
GGTGGCACTT TTCGGGGAAA TGTGCGCGGA ACCCCTATTT GTTTATTTTT CTAAATACAT TCAAATATGT ATCCGCTCAT
GAGACAATAA CCCTGATAAA TGCTTCAATA ATATTGAAAA AGGAAGAGTA TGAGTATTCA ACATTTCCGT GTCGCCCTTA
TTCCCTTTTT TGCGGCATTT TGCCTTCCTG TTTTTGCTCA CCCAGAAACG CTGGTGAAAG TAAAAGATGC TGAAGATCAG
TTGGGTGCAC GAGTGGGTTA CATCGAACTG GATCTCAACA GCGGTAAGAT CCTTGAGAGT TTTCGCCCCG AAGAACGTTC
TCCAATGATG AGCACTTTTA AAGTTCTGCT ATGTGGCGCG GTATTATCCC GTGTTGACGC CGGGCAAGAG CAACTCGGTC
GCCGCATACA CTATTCTCAG AATGACTTGG TTGAGTACTC ACCAGTCACA GAAAAGCATC TTACGGATGG CATGACAGTA
AGAGAATTAT GCAGTGCTGC CATAACCATG AGTGATAACA CTGCGGCCAA CTTACTTCTG ACAACGATCG GAGGACCGAA
GGAGCTAACC GCTTTTTTGC ACAACATGGG GGATCATGTA ACTCGCCTTG ATCGTTGGGA ACCGGAGCTG AATGAAGCCA
TACCAAACGA CGAGCGTGAC ACCACGATGC CTGTAGCAAT GGCAACAACG TTGCGCAAAC TATTAACTGG CGAACTACTT
ACTCTAGCTT CCCGGCAACA ATTAATAGAC TGGATGGAGG CGGATAAAGT TGCAGCACA CTTCTGCGCT CGGCCCTTCC
GGCTGGCTGG TTTATTGCTG ATAAATCTGG AGCCGGTGAG CGTGGGTCTC GCGGTATCAT TGCAGCACTG GGGCCAGATG
GTAAGCCCTC CCGTATCGTA GTTATCTACA CGACGGGGAG TCAGGCAACT ATGGATGAAC GAAATAGACA GATCGCTGAG
ATAGGTGCCT CACTGATTAA GCATTGGTAA CTGTCAGACC AAGTTTACTC ATATATACTTT TAGATTGATT TACCCCGGTT
GATAATCAGA AAAGCCCCAA AAACAGGAAG ATTGTATAAG CAAATATTTA AATTGTAAAC GTTAATAATT TGTTAAAATT
CGCGTTAAAT TTTTGTTAAA TCAGCTCATT TTTTAACCAA TAGGCCGAAA TCGGCAAAAT CCCTTATAAA TCAAAAGAAT
AGCCCGAGAT AGGGTTGAGT GTTGTTCCAG TTTGGAACAA GAGTCCACTA TTAAAGAACG TGGACTCCAA CGTCAAAGGG
CGAAAAACCG TCTATCAGGG CGATGGCCCA CTACGTGAAC CATCACCCAA ATCAAGTTTT TTGGGGTCGA GGTGCCGTAA
AGCACTAAAT CGGAACCCTA AAGGGAGCCC CCGATTTAGA GCTTGACGGG GAAAGCGAAC GTGGCGAGAA AGGAAGGGAA
GAAAGCGAAA GGAGCGGGCG CTAGGGCGCT GGCAAGTGTA GCGGTCACGC TGCGCGTAAC CACCACACCC GCCGCGCTTA
ATGCGCCGCT ACAGGGCGCG TAAAAGGATC TAGGTGAAGA TCCTTTTTGA TAATCTCATG ACCAAAATCC CTTAACGTGA
GTTTTCGTTC CACTGAGCGT CAGACCCCGT AGAAAAGATC AAAGGATCTT CTTGAGATCC TTTTTTTCTG CGCGTAATCT
GGTGCTTGCA AACAAAAAAA CCACCGCTAC CAGCGGTGGT TTGTTTGCCG GATCAAGAGC TACCAACTCT TTTTCCGAAG
GTAACTGGCT TCAGCAGAGC GCAGATACCA AATACTGTTC TTCTAGTGTA GCCGTAGTTA GGCCACCACT TCAAGAACTC
TGTAGCACCG CCTACATACC TCGCTCTGCT AATCCTGTTA CCAGTGGCTG CTGCCAGTGG CGATAAGTCG TGTCTTACCG
GGTTGGACTC AAGACGATAG TTACCGGATA AGGCGCAGCG GTCGGGCTGA ACGGGGGGTT CGTGCACACA GCCCAGCTTG
GAGCGAACGA CCTACACCGA ACTGAGATAC CTACAGCGTG AGCTATGAGA AAGCGCCACG CTTCCCGAAG GGAGAAAGGC
GGACAGGTAT CCGGTAAGCG GCAGGGTCGG AACAGGAGAG CGCACGAGGG AGCTTCCAGG GGGAAACGCC TGGTATCTTT
ATAGTCCTGT CGGGTTTCGC CACCTCTGAC TTGAGCGTCG ATTTTTGTGA TGCTCGTCAG GGGGGCGGAG CCTATGGAAA
AACGCCAGCA ACGCGGCCTT TTTACGGTTC CTGGCCTTTT GCTGGCCTTT TGCTCACATG TAATGTGAGT TAGCTCACTC
ATTAGGCACC CCAGGCTTTA CACTTTATGC TTCCGGCTCG TATGTTGTGT GGAATTGTGA GCGGATAACA ATTTCACACA
GGAAACAGCT ATGACCATGA TTACGCCAAG CTACGTAATA CGACTCACTA GGCGGCCGCG TTTAAACAAT GTGCTCCTCT
TTGCTTGCT TCCGCGGGCC AAGCAGACA AGAACCAGTT GACGTCAAGC TTCCCGGGAC GCGTGCTAGC GGCGCGCCGA
ATTCCTGCAG GATTCGAGGG CCCCTGCAGG TCAATTCTAC CGGGTAGGGG AGCGCTTTT CCAAGGCAG TCTGAGCAT
GCGCTTTAGC AGCCCCGCTG GCACTTGGCG CTACACAAGT GGCCTCTGGC CTCGCACACA TTCCACATCC ACCGGTAGCG
CCAACCGGCT CCGTTCTTTG GTGGCCCCTT CGCGCCACCT TCTACTCCTC CCCTAGTCAG GAAGTTCCCC CCCGCCCCGC
AGCTCGCGTC GTGCAGGACG TGACAAATGG AAGTAGCACG TCTCACTAGT CTCGTGCAGA TGGACAGCAC CGCTGAGCAA
TGGAAGCGGG TAGGCCTTTG GGGCAGCGGC CAATAGCAGC TTTGCTCCTT CGCTTTCTGG GCTCAGAGGC TGGGAAGGGG
```

FIGURE 3B1

```
TGGGTCCGGG GGCGGGCTCA GGGGCGGGCT CAGGGGCGGG GCGGGCGCGA AGGTCCTCCC GAGGCCCGGC ATTCTCGCAC
GCTTCAAAAG CGCACGTCTG CCGCGCTGTT CTCCTCTTCC TCATCTCCGG GCCTTTCGAC CTGCAGCCAA TATGGGATCG
GCCATTGAAC AAGATGGATT GCACGCAGGT TCTCCGGCCG CTTGGGTGGA GAGGCTATTC GGCTATGACT GGGCACAACA
GACAATCGGC TGCTCTGATG CCGCCGTGTT CCGGCTGTCA GCGCAGGGGC GCCCGGTTCT TTTTGTCAAG ACCGACCTGT
CCGGTGCCCT GAATGAACTG CAGGACGAGG CAGCGCGGCT ATCGTGGCTG GCCACGACGG GCGTTCCTTC CGCAGCTGTG
CTCGACGTTG TCACTGAAGC GGGAAGGGAC TGGCTGCTAT TGGGCGAAGT GCCGGGGCAG GATCTCCTGT CATCTCACCT
TGCTCCTGCC GAGAAAGTAT CCATCATGGC TGATGCAATG CGGCGGCTGC ATACGCTTGA TCCGGCTACC TGCCCATTCG
ACCACCAAGC GAAACATCGC ATCGAGCGAG CACGTACTCG GATGGAAGCC GGTCTTGTCG ATCAGGATGA TCTGGACGAA
GAGCATCAGG GGCTCGCGCC AGCCGAACTG TTCGCCAGGC TCAAGGCGCG CATGCCGGAC GGCGATGATC TCGTCGTGAC
CCATGGCGAT GCCTGCTTGC CGAATATCAT GGTGGAAAAT GGCCGCTTTT CTGGATTCAT CGACTGTGGC CGGCTGGGTG
TGGCGGACCG CTATCAGGAC ATAGCGTTGG CTACCCGTGA TATTGCTGAA GAGCTTGGCG GCGAATGGGC TGACCGCTTC
CTCGTGCTTT ACGGTATCGC CGCTCCCGAT TCGCAGCGCA TCGCCTTCTA TCGCCTTCTT GACGAGTTCT TCTGAGGGGA
TCGATCCGTC CTGTAAGTCT GCAGAAATTG ATGATCTATT AAACAATAAA GATGTCCACT AAAATGGAAG TTTTTCCTGT
CATACTTTGT TAAGAAGGGT GAGAACAGAG TACCTACATT TTGAATGGAA GGATTGGAGC TACGGGGTG GGGGTGGGGT
GGGATTAGAT AAATGCCTGC TCTTTACTGA AGGCTCTTTA CTATTGCTTT ATGATAATGT TTCATAGTTG GATATCATAA
TTTAAACAAG CAAAACCAAA TTAAGGGCCA GCTCATTCCT CCCACTCATG ATCTATAGAT CTATAGATCT CTCGTGGGAT
CATTGTTTTT CTCTTGATTC CCACTTTGTG GTTCTAAGTA CTGTGGTTTC CAAATGTGTC AGTTTCATAG CCTGAAGAAC
GAGATCAGCA GCCTCTGTTC CACATACACT TCATTCTCAG TATTGTTTTG CCAAGTTCTA ATTCCATCAG AAGCTGACTC
TAGATCTGGA TCCGGCCAGC TAGGCCGTCG ACCTCGAGTG ATCAGGTACC AAGGTCCTCG CTCTGTGTCC GTTGAGCTCG
ACGACACAGG ACACGCAAAT TAATTAAGGC CGGCCCGTAC CCTCTAGTCA AGGCCTTAAG TGAGTCGTAT TACGGACTGG
CGGTCGTTTT ACAACGTCGT GACTGGGAAA ACCCTGGCGT TACCCAACTT AATCGCCTTG CAGCACATCC CCCTTTCGCC
AGCTGGCGTA ATAGCGAAGA GGCCCGCACC GATCGCCCTT CCCAACAGTT GCGCAGCCTG AATGGCGAAT GGCGCTTCGC
TTGGTAATAA AGCCCGCTTC GGCGGGCTTT TTTTT
```

FIGURE 3B2

| Annealing site | Sequence | | | Sequence after digestion | |
|---|---|---|---|---|---|
| 1 | 5'<br>3' | tgtgctcctctttggcttgcttccaa...<br>acacgaggagaaaccgaacgaaggtt... | 3'<br>5' | 5' tgtgctcctctttggcttgcttccaa...<br>3'                          tt... | 3'<br>5' |
| 2 | 5'<br>3' | ctggttcttgtctgacttggcccaa...<br>gaccaagaacagaccgaaccggggtt... | 3'<br>5' | 5' ctggttcttgtctgacttggcccaa...<br>3'                          tt... | 3'<br>5' |
| 3 | 5'<br>3' | ggtcctcgctctgtgtccgttgaa...<br>ccaggagcgagacacaggcaactt... | 3'<br>5' | 5' ggtcctcgctctgtgtccgttgaa...<br>3'                        tt... | 3'<br>5' |
| 4 | 5'<br>3' | tttgcgtgtcctgtgtcgtcgaa...<br>aaacgcacaggacacagcagctt... | 3'<br>5' | 5' tttgcgtgtcctgtgtcgtcgaa...<br>3'                       tt... | 3'<br>5' |

FIGURE 4

| Annealing site | Sequence | | | Sequence after digestion | | |
|---|---|---|---|---|---|---|
| 1 | AAtgtgctcctcttggcttgcttCCGC<br>Ttacacgaggagaaaccgaacgaagg | 3'<br>5' | | AA<br>Ttacacgaggagaaaccgaacgaagg | 5'<br>3' | 3'<br>5' |
| 2 | AActggttcttgtctgctggCCCGC<br>Ttgaccaagaacagaccgaacccggg | 3'<br>5' | | AA<br>Ttgaccaagaacagaccgaacccggg | 5'<br>3' | 3'<br>5' |
| 3 | AAggtcctcgctctgtgtccgttGAGCT<br>Ttccaggagcgagacacaggcaac | 3'<br>5' | | AA<br>Ttccaggagcgagacacaggcaac | 5'<br>3' | 3'<br>5' |
| 4 | AAtttgcgtgtcctgtcgtcGAGCT<br>Ttaaacgcacaggacacagcagc | 3'<br>5' | | AA<br>Ttaaacgcacaggacacagcagc | 5'<br>3' | 3'<br>5' |

FIGURE 5

| Oligo# | Sequence (5' to 3') |
|---|---|
| 174 | ATGACCGCTCAGGAAACCTGTTGCA |
| 180 | ATAGGCATAGTAGGCCAGCTTGAGG |
| | |
| 454 | tgtgctcctctttggcttgcttccAATTAACCCTCACTAAAGGGAACGAAT |
| 463 | ctggttcttgtctggcttggcccaaTGCAACAGGTTTCCTGAGCGGTCAT |
| | |
| 464 | ggtcctcgctctgtgtccgttgaaCCTCAAGCTGGCCTACTATGCCTAT |
| 42 | tttgcgtgtcctgtgtcgtcgaaCGACTAATACGACTCACTATAGGGCG |
| | |
| 151 | GCCAATGGACTCTTAGTTTTGGAAC |
| 155 | GTTCTGGCAAACAAATTCGGCGCAC |
| | |
| 454 | tgtgctcctctttggcttgcttccAATTAACCCTCACTAAAGGGAACGAAT |
| 465 | ctggttcttgtctggcttggcccaaGTTCCAAAACTAAGAGTCCATTGGC |
| | |
| 466 | ggtcctcgctctgtgtccgttgaaGTGCGCCGAATTTGTTTGCCAGAAC |
| | |
| 1 | GAACCTTGGTGTGCCAAGTTACTTC |
| 2 | GAACTTTGGCTGAACCCCTTGTTCT |
| | |
| 41 | tgtgctcctctttggcttgcgttgaaCGACTAATACGACTCACTATAGGGCG |
| 38 | ctggttcttgtctggcttggcccaaGAAGTAACTTGGCACACCAAGGTTC |
| | |
| 40 | ggtcctcgctctgtgtccgttgaAGAACAAGGGGTTCAGCCAAAGTTC |
| 37 | tttgcgtgtcctgtgtcgtcgAATTAACCCTCACTAAAGGGAACGAAT |
| | |
| 540 | ATGCCGGATCTCCTACTACTGGGCC |
| 546 | TGTCATAGTAGACAGCGATGGAACG |
| | |
| 445 | GACAAGAACCAGTTGACGTCAAGCTTCCCGGGACGCGTGCTAGCGGCGCGCCG |
| 667 | ctggttcttgtctggcttggcccaaGGCCCAGTAGTAGGAGATCCGGCAT |
| | |
| 668 | ggtcctcgctctgtgtccgttgaaCGTTCCATCGCTGTCTACTATGACA |
| | |
| 907 | ctggttcttgtctggcttggcccaaAAAGCCGACAGCCACGCTCACAAGC |
| 908 | ggtcctcgctctgtgtccgttgaaGCCAATGCCACAGAGACAGAATGT |
| | |
| 1157 | ctggttcttgtctggcttggcccaaGTTGGATCCTCTCCAAGGCCCCATCT |
| 1158 | ggtcctcgctctgtgtccgttgaaCTCCAGTGCCGAGTGTGTGGGACAG |

Figure 8

SEQUENCE LISTING

<160> NUMBER OF SEQ ID NOS: 44

<210> SEQ ID NO 1
<211> LENGTH: 4768
<212> TYPE: DNA
<213> ORGANISM: Plasmid vector

<400> SEQUENCE: 1

```
gttaactacg tcaggtggca cttttcgggg aaatgtgcgc ggaacccta tttgtttatt      60
tttctaaata cattcaaata tgtatccgct catgagacaa taaccctgat aaatgcttca     120
ataatattga aaaggaaga gtatgagtat tcaacatttc cgtgtcgccc ttattccctt     180
ttttgcggca ttttgccttc ctgttttgc tcacccagaa acgctggtga agtaaaaga      240
tgctgaagat cagttgggtg cacgagtggg ttacatcgaa ctggatctca acagcggtaa    300
gatccttgag agtttttcgcc ccgaagaacg ttctccaatg atgagcactt ttaaagttct    360
gctatgtggc gcggtattat cccgtgttga cgccgggcaa gagcaactcg gtcgccgcat    420
acactattct cagaatgact tggttgagta ctcaccagtc acagaaaagc atcttacgga    480
tggcatgaca gtaagagaat tatgcagtgc tgccataacc atgagtgata acactgcggc    540
caacttactt ctgacaacga tcggaggacc gaaggagcta accgcttttt tgcacaacat    600
gggggatcat gtaactcgcc ttgatcgttg ggaaccggag ctgaatgaag ccataccaaa    660
cgacgagcgt gacaccacga tgcctgtagc aatggcaaca acgttgcgca aactattaac    720
tggcgaacta cttactctag cttcccggca acaattaata gactggatgg aggcggataa    780
agttgcagga ccacttctgc gctcggccct tccggctggc tggtttattg ctgataaatc    840
tggagccggt gagcgtgggt ctcgcggtat cattgcagca ctggggccag atggtaagcc    900
ctcccgtatc gtagttatct acacgacggg gagtcaggca actatggatg aacgaaatag    960
acagatcgct gagataggtg cctcactgat taagcattgg taactgtcag accaagttta   1020
ctcatatata ctttagattg atttaccccg gttgataatc agaaaagccc caaaaacagg   1080
aagattgtat aagcaaatat ttaaattgta aacgttaata ttttgttaaa attcgcgtta   1140
aatttttgtt aaatcagctc attttttaac caataggccg aaatcggcaa aatcccttat   1200
aaatcaaaag aatagcccga gatagggttg agtgttgttc cagtttggaa caagagtcca   1260
ctattaaaga acgtggactc caacgtcaaa gggcgaaaaa ccgtctatca gggcgatggc   1320
ccactacgtg aaccatcacc caaatcaagt tttttggggt cgaggtgccg taaagcacta   1380
aatcggaacc ctaaagggag cccccgattt agagcttgac ggggaaagcg aacgtggcga   1440
gaaaggaagg gaagaaagcg aaaggagcgg gcgctagggc gctggcaagt gtagcggtca   1500
cgctgcgcgt aaccaccaca cccgccgcgc ttaatgcgcc gctacagggc gcgtaaaagg   1560
atctaggtga agatcctttt tgataatctc atgaccaaaa tcccttaacg tgagttttcg   1620
ttccactgag cgtcagaccc cgtagaaaag atcaaaggat cttcttgaga tcctttttt    1680
ctgcgcgtaa tctgctgctt gcaaacaaaa aaaccaccgc taccagcggt ggtttgtttg   1740
```

-continued

```
ccggatcaag agctaccaac tcttttccg aaggtaactg gcttcagcag agcgcagata      1800
ccaaatactg ttcttctagt gtagccgtag ttaggccacc acttcaagaa ctctgtagca      1860
ccgcctacat acctcgctct gctaatcctg ttaccagtgg ctgctgccag tggcgataag      1920
tcgtgtctta ccgggttgga ctcaagacga tagttaccgg ataaggcgca gcggtcgggc      1980
tgaacggggg gttcgtgcac acagcccagc ttggagcgaa cgacctacac cgaactgaga      2040
tacctacagc gtgagctatg agaaagcgcc acgcttcccg aagggagaaa ggcggacagg      2100
tatccggtaa cgcaggggt cggaacagga gagcgcacga gggagcttcc aggggaaac       2160
gcctggtatc tttatagtcc tgtcgggttt cgccacctct gacttgagcg tcgatttttg      2220
tgatgctcgt cagggggcg gagcctatgg aaaaacgcca gcaacgcggc cttttacgg       2280
ttcctggcct tttgctggcc ttttgctcac atgtaatgtg agttagctca ctcattaggc      2340
accccaggct ttacactta tgcttccggc tcgtatgttg tgtggaattg tgagcggata      2400
acaatttcac acaggaaaca gctatgacca tgattacgcc aagctacgta atacgactca      2460
ctaggcggcc gcgtttaaac aatgtgctcc tctttggctt gcttccgcgg gccaagccag      2520
acaagaacca gttgacgtca gcttcccgg gacgcgtgct agcggcgcgc cgaattcctg        2580
caggattcga gggcccctgc aggtcaattc taccgggtag gggaggcgct tttcccaagg      2640
cagtctggag catgcgcttt agcagccccg ctggcacttg cgctacaca agtggcctct       2700
ggcctcgcac acattccaca tccaccggta gcgccaaccg ctccgttct ttggtggccc       2760
cttcgcgcca ccttctactc ctccctagt caggaagttc ccccccgccc cgcagctcgc       2820
gtcgtgcagg acgtgacaaa tggaagtagc acgtctcact agtctcgtgc agatggacag      2880
caccgctgag caatgaagc gggtaggcct ttggggcagc ggccaatagc agctttgctc       2940
cttcgctttc tgggctcaga ggctgggaag gggtgggtcc gggggcgggc tcaggggcgg      3000
gctcaggggc gggcgggcg cgaaggtcct cccgaggccc ggcattctcg cacgcttcaa       3060
aagcgcacgt ctgccgcgct gttctcctct tcctcatctc cgggcctttc gacctgcagc      3120
caatatggga tcgccattg aacaagatgg attgcacgca ggttctccgg ccgcttgggt       3180
ggagaggcta ttcggctatg actgggcaca acagacaatc ggctgctctg atgccgccgt      3240
gttccgctg tcagcgcagg ggcgcccggt tctttttgtc aagaccgacc tgtccggtgc       3300
cctgaatgaa ctgcaggacg aggcagcgcg gctatcgtgg ctggccacga cgggcgttcc      3360
ttgcgcagct gtgctcgacg ttgtcactga agcgggaagg gactggctgc tattgggcga      3420
agtgccgggg caggatctcc tgtcatctca ccttgctcct gccgagaaag tatccatcat      3480
ggctgatgca atgcggcggc tgcatacgct tgatccggct acctgcccat tcgaccacca      3540
agcgaaacat cgcatcgagc gagcacgtac tcggatggaa gccggtcttg tcgatcagga      3600
tgatctggac gaagagcatc aggggctcgc gccagccgaa ctgttcgcca ggctcaaggc      3660
gcgcatgccc gacggcgatg atctcgtcgt gacccatggc gatgcctgct tgccgaatat      3720
catggtggaa aatggccgct tttctggatt catcgactgt ggccggctgg gtgtggcgga      3780
ccgctatcag gacatagcgt tggctacccg tgatattgct gaagagcttg gcggcgaatg      3840
ggctgaccgc ttcctcgtgc tttacggtat cgccgctccc gattcgcagc gcatcgcctt      3900
ctatcgcctt cttgacgagt tcttctgagg ggatcgatcc gtcctgtaag tctgcagaaa      3960
ttgatgatct attaaacaat aaagatgtcc actaaaatgg aagttttcc tgtcatactt      4020
tgttaagaag ggtgagaaca gagtacctac attttgaatg gaaggattgg agctacgggg      4080
```

```
gtgggggtgg ggtgggatta gataaatgcc tgctctttac tgaaggctct ttactattgc    4140
tttatgataa tgtttcatag ttggatatca taatttaaac aagcaaaacc aaattaaggg    4200
ccagctcatt cctcccactc atgatctata gatctataga tctctcgtgg gatcattgtt    4260
tttctcttga ttcccacttt gtggttctaa gtactgtggt ttccaaatgt gtcagtttca    4320
tagcctgaag aacgagatca gcagcctctg ttccacatac acttcattct cagtattgtt    4380
ttgccaagtt ctaattccat cagaagctga ctctagatct ggatccggcc agctaggccg    4440
tcgacctcga gtgatcaggt accaaggtcc tcgctctgtg tccgttgagc tcgacgacac    4500
aggacacgca aattaattaa ggccggcccg taccctctag tcaaggcctt aagtgagtcg    4560
tattacggac tggccgtcgt tttacaacgt cgtgactggg aaaaccctgg cgttacccaa    4620
cttaatcgcc ttgcagcaca tccccctttc gccagctggc gtaatagcga gaggcccgc    4680 accgatcgcc cttcccaaca gttgcgcagc ctgaatggcg aatggcgctt cgcttggtaa    4740
taaagcccgc ttcggcgggc ttttttt                                       4768

<210> SEQ ID NO 2
<211> LENGTH: 6355
<212> TYPE: DNA
<213> ORGANISM: Plasmid vector

<400> SEQUENCE: 2
gtttaatagt aatcaattac gggtcatta gttcatagcc catatatgga gttccgcgtt      60
acataactta cggtaaatgg cccgcctggc tgaccgccca acgacccccg cccattgacg     120
tcaataatga cgtatgttcc catagtaacg ccaataggga ctttccattg acgtcaatgg     180
gtggagtatt tacggtaaac tgcccacttg gcagtacatc aagtgtatca tatgccaagt     240
acgcccccta ttgacgtcaa tgacggtaaa tggcccgcct ggcattatgc ccagtacatg     300 acctatggg actttcctac ttggcagtac atctacgtat tagtcatcgc tattaccatg      360
gtgatgcggt tttggcagta catcaatggg cgtggatagc ggtttgactc acggggattt     420
ccaagtctcc accccattga cgtcaatggg agtttgtttt ggcaccaaaa tcaacgggac     480
tttccaaaat gtcgtaacaa ctccgcccca ttgacgcaaa tgggcggtag gcgtgtacgg     540
tgggaggtct atataagcag agctggttta gtgaaccgtc agatccgcta gcgctaccgg     600
tcgccaccat ggtgagcaag ggcgaggagc tgttcaccgg ggtggtgccc atcctggtcg     660
agctggacgg cgacgtaaac ggccacaagt tcagcgtgtc cggcgagggc gagggcgatg     720
ccacctacgg caagctgacc ctgaagttca tctgcaccac cggcaagctg cccgtgccct     780
ggcccaccct cgtgaccacc ctgacctacg gcgtgcagtg cttcagccgc taccccgacc     840
acatgaagca gcacgacttc ttcaagtccg ccatgcccga aggctacgtc caggagcgca     900
ccatcttctt caaggacgac ggcaactaca agacccgcgc cgaggtgaag ttcgagggcg     960
acaccctggt gaaccgcatc gagctgaagg gcatcgactt caaggaggac ggcaacatcc    1020
tggggcacaa gctggagtac aactacaaca gccacaacgt ctatatcatg gccgacaagc    1080
agaagaacgg catcaaggtg aacttcaaga tccgccacaa catcgaggac ggcagcgtgc    1140
agctcgccga ccactaccag cagaacaccc ccatcggcga cggccccgtg ctgctgcccg    1200
acaaccacta cctgagcacc cagtccgccc tgagcaaaga ccccaacgag aagcgcgatc    1260
acatggtcct gctggagttc gtgaccgccg ccgggatcac tctcggcatg gacgagctgt    1320
acaagtccgg actcagatcc accgatcta gataactgat cataatcagc cataccacat    1380
ttgtagaggt tttacttgct ttaaaaaacc tcccacacct cccctgaac ctgaaacata    1440
```

```
aaatgaatgc aattgttgtt gttaacttgt ttattgcagc ttataatggt tacaaataaa   1500
gcaatagcat cacaaatttc acaaataaag cattttttc  actgcattct agttgtggtt   1560
tgtccaaact catcaatgta tcttaacgcg aactacgtca ggtggcactt ttcgggaaa    1620 tgtgcgcgga accctatttt gtttattttt ctaaatacat tcaaatatgt atccgctcat   1680
gagacaataa ccctgataaa tgcttcaata atattgaaaa aggaagagta tgagtattca   1740
acatttccgt gtcgccctta ttcccttttt tgcggcattt tgccttcctg ttttgctca    1800 cccagaaacg ctggtgaaag taaaagatgc tgaagatcag ttgggtgcac gagtgggtta   1860
catcgaactg gatctcaaca gcggtaagat ccttgagagt tttcgccccg aagaacgttc   1920
tccaatgatg agcacttta  aagttctgct atgtggcgcg gtattatccc gtgttgacgc   1980
cgggcaagag caactcggtc gccgcataca ctattctcag aatgacttgg ttgagtactc   2040
accagtcaca gaaaagcatc ttacggatgg catgacagta agagaattat gcagtgctgc   2100
cataaccatg agtgataaca ctgcggccaa cttacttctg acaacgatcg aggaccgaa    2160 ggagctaacc gcttttttgc acaacatggg ggatcatgta actcgccttg atcgttggga   2220
accggagctg aatgaagcca taccaaacga cgagcgtgac accacgatgc ctgtagcaat   2280
ggcaacaacg ttgcgcaaac tattaactgg cgaactactt actctagctt cccggcaaca   2340
attaatagac tggatggagg cggataaagt tgcaggacca cttctgcgct cggcccttcc   2400
ggctggctgg tttattgctg ataaatctgg agccggtgag cgtgggtctc gcggtatcat   2460
tgcagcactg gggccagatg gtaagccctc ccgtatcgta gttatctaca cgacggggag   2520
tcaggcaact atggatgaac gaaatagaca gatcgctgag ataggtgcct cactgattaa   2580
gcattggtaa ctgtcagacc aagtttactc atatatactt tagattgatt taccccggtt   2640
gataatcaga aaagccccaa aacaggaag  attgtataag caaatattta aattgtaaac   2700 gttaatatt  tgttaaaatt cgcgttaaat tttgttaaa  tcagctcatt ttttaaccaa   2760
taggccgaaa tcggcaaaat cccttataaa tcaaaagaat agcccgagat agggttgagt   2820
gttgttccag tttggaacaa gagtccacta ttaaagaacg tggactccaa cgtcaaaggg   2880
cgaaaaaccg tctatcaggg cgatggccca ctacgtgaac catcacccaa atcaagtttt   2940
ttggggtcga ggtgccgtaa agcactaaat cggaaccta  agggagccc  ccgatttaga   3000 gcttgacggg gaaagcgaac gtggcgagaa aggaagggaa gaaagcgaaa ggagcgggcg   3060
ctagggcgct ggcaagtgta gcggtcacgc tgcgcgtaac caccacaccc gccgcgctta   3120
atgcgccgct acagggcgcg taaaaggatc taggtgaaga tccttttga  taatctcatg   3180 accaaaatcc cttaacgtga gttttcgttc cactgagcgt cagacccgt  agaaaagatc   3240 aaaggatctt cttgagatcc tttttttctg cgcgtaatct gctgcttgca aacaaaaaaa   3300
ccaccgctac cagcggtggt ttgtttgccg gatcaagagc taccaactct ttttccgaag   3360
gtaactggct tcagcagagc gcagatacca aatactgttc ttctagtgta gccgtagtta   3420
ggccaccact tcaagaactc tgtagcaccg cctacatacc tcgctctgct aatcctgtta   3480
ccagtggctg ctgccagtgg cgataagtcg tgtcttaccg ggttggactc aagacgatag   3540
ttaccggata aggcgcagcg gtcgggctga acggggggtt cgtgcacaca gcccagcttg   3600
gagcgaacga cctacaccga actgagatac ctacagcgtg agctatgaga aagcgccacg   3660
cttcccgaag ggagaaaggc ggacaggtat ccggtaagcg gcagggtcgg aacaggagag   3720
cgcacgaggg agcttccagg gggaaacgcc tggtatcttt atagtcctgt cgggtttcgc   3780
```

```
cacctctgac ttgagcgtcg attttttgtga tgctcgtcag gggggcggag cctatggaaa    3840
aacgccagca acgcggcctt tttacggttc ctggccttttt gctggccttt tgctcacatg    3900
taatgtgagt tagctcactc attaggcacc ccaggcttta cactttatgc ttccggctcg    3960
tatgttgtgt ggaattgtga gcggataaca atttcacaca ggaaacagct atgaccatga    4020
ttacgccaag ctacgtaata cgactcacta ggcggccgcg tttaaacaat gtgctcctct    4080
ttggcttgct tccgcgggcc aagccagaca agaaccagtt gacgtcaagc ttcccgggac    4140
gcgtgctagc ggcgcgccga attcctgcag gattcgaggg cccctgcagg tcaattctac    4200
cgggtagggg aggcgctttt cccaaggcag tctggagcat gcgctttagc agccccgctg    4260
gcacttggcg ctacacaagt ggcctctggc ctcgcacaca ttccacatcc accggtagcg    4320
ccaaccggct ccgttctttg gtggcccctt cgcgccacct tctactcctc ccctagtcag    4380
gaagttcccc cccgccccgc agctcgcgtc gtgcaggacg tgacaaatgg aagtagcacg    4440
tctcactagt ctcgtgcaga tggacagcac cgctgagcaa tggaagcggg taggcctttg    4500 ggcagcggc caatagcagc tttgctcctt cgctttctgg gctcagaggc tgggaagggg    4560
tgggtccggg ggcgggctca ggggcgggct caggggcggg gcgggcgcga aggtcctccc    4620
gaggcccggc attctcgcac gcttcaaaag cgcacgtctg ccgcgctgtt ctcctcttcc    4680
tcatctccgg gcctttcgac ctgcagccaa tatgggatcg gccattgaac aagatggatt    4740
gcacgcaggt tctccggccg cttgggtgga gaggctattc ggctatgact gggcacaaca    4800
gacaatcggc tgctctgatg ccgccgtgtt ccggctgtca gcgcaggggc gcccggttct    4860
ttttgtcaag accgacctgt ccggtgccct gaatgaactg caggacgagg cagcgcggct    4920
atcgtggctg gccacgacgg gcgttccttg cgcagctgtg ctcgacgttg tcactgaagc    4980
gggaagggac tggctgctat tgggcgaagt gccggggcag gatctcctgt catctcacct    5040
tgctcctgcc gagaaagtat ccatcatggc tgatgcaatg cggcggctgc atacgcttga    5100
tccggctacc tgcccattcg accaccaagc gaaacatcgc atcgagcgag cacgtactcg    5160
gatggaagcc ggtcttgtcg atcaggatga tctggacgaa gagcatcagg gctcgcgcc    5220 agccgaactg ttcgccaggc tcaaggcgcg catgcccgac ggcgatgatc tcgtcgtgac    5280
ccatggcgat gcctgcttgc cgaatatcat ggtggaaaat ggccgctttt ctggattcat    5340
cgactgtggc cggctgggtg tggcggaccg ctatcaggac atagcgttgg ctacccgtga    5400
tattgctgaa gagcttggcg gcgaatgggc tgaccgcttc ctcgtgcttt acggtatcgc    5460
cgctcccgat tcgcagcgca tcgccttcta tcgccttctt gacgagttct tctgagggga    5520
tcgatccgtc ctgtaagtct gcagaaattg atgatctatt aaacaataaa gatgtccact    5580
aaaatggaag ttttttcctgt catactttgt taagaagggt gagaacagag tacctacatt    5640
ttgaatggaa ggattggagc tacggggtg ggggtggggt gggattagat aaatgcctgc    5700
tctttactga aggctcttta ctattgcttt atgataatgt ttcatagttg gatatcataa    5760
tttaaacaag caaaaccaaa ttaagggcca gctcattcct cccactcatg atctatagat    5820
ctatagatct ctcgtgggat cattgttttt ctcttgattc ccactttgtg gttcaagta    5880 ctgtggtttc caaatgtgtc agtttcatag cctgaagaac gagatcagca gcctctgttc    5940
cacatacact tcattctcag tattgttttg ccaagttcta attccatcag aagctgactc    6000
tagatctgga tccggccagc taggccgtcg acctcgagtg atcaggtacc aaggtcctcg    6060
ctctgtgtcc gttgagctcg acgacacagg acacgcaaat taattaaggc cggcccgtac    6120
cctctagtca aggccttaag tgagtcgtat tacggactgg ccgtcgtttt acaacgtcgt    6180
```

```
gactgggaaa accctggcgt tacccaactt aatcgccttg cagcacatcc cccttttcgcc        6240 agctggcgta atagcgaaga ggcccgcacc gatcgccctt cccaacagtt gcgcagcctg        6300
aatggcgaat ggcgcttcgc ttggtaataa agcccgcttc ggcgggcttt ttttt            6355

<210> SEQ ID NO 3
<211> LENGTH: 28
<212> TYPE: DNA
<213> ORGANISM: Plasmid vector

<400> SEQUENCE: 3
aatgtgctcc tctttggctt gcttccgc                                          28

<210> SEQ ID NO 4
<211> LENGTH: 26
<212> TYPE: DNA
<213> ORGANISM: Plasmid vector

<400> SEQUENCE: 4
ggaagcaagc caaagaggag cacatt                                            26

<210> SEQ ID NO 5
<211> LENGTH: 27
<212> TYPE: DNA
<213> ORGANISM: Plasmid vector

<400> SEQUENCE: 5
aactggttct tgtctggctt ggcccgc                                           27

<210> SEQ ID NO 6
<211> LENGTH: 25
<212> TYPE: DNA
<213> ORGANISM: Plasmid vector

<400> SEQUENCE: 6
gggccaagcc agacaagaac cagtt                                             25

<210> SEQ ID NO 7
<211> LENGTH: 28
<212> TYPE: DNA
<213> ORGANISM: Plasmid vector

<400> SEQUENCE: 7
aaggtcctcg ctctgtgtcc gttgagct                                          28

<210> SEQ ID NO 8
<211> LENGTH: 24
<212> TYPE: DNA
<213> ORGANISM: Plasmid vector

<400> SEQUENCE: 8
caacggacac agagcgagga cctt                                              24

<210> SEQ ID NO 9
<211> LENGTH: 27
<212> TYPE: DNA
<213> ORGANISM: Plasmid vector

<400> SEQUENCE: 9
aatttgcgtg tcctgtgtcg tcgagct                                           27

<210> SEQ ID NO 10
```

-continued

```
<211> LENGTH: 23
<212> TYPE: DNA
<213> ORGANISM: Plasmid vector

<400> SEQUENCE: 10
cgacgacaca ggacacgcaa att                                             23

<210> SEQ ID NO 11
<211> LENGTH: 26
<212> TYPE: DNA
<213> ORGANISM: Plasmid vector

<400> SEQUENCE: 11
tgtgctcctc tttggcttgc ttccaa                                          26

<210> SEQ ID NO 12
<211> LENGTH: 26
<212> TYPE: DNA
<213> ORGANISM: Plasmid vector

<400> SEQUENCE: 12
ttggaagcaa gccaaagagg agcaca                                          26

<210> SEQ ID NO 13
<211> LENGTH: 25
<212> TYPE: DNA
<213> ORGANISM: Plasmid vector

<400> SEQUENCE: 13
ctggttcttg tctggcttgg cccaa                                           25

<210> SEQ ID NO 14
<211> LENGTH: 25
<212> TYPE: DNA
<213> ORGANISM: Plasmid vector

<400> SEQUENCE: 14
ttgggccaag ccagacaaga accag                                           25

<210> SEQ ID NO 15
<211> LENGTH: 24
<212> TYPE: DNA
<213> ORGANISM: Plasmid vector

<400> SEQUENCE: 15
ggtcctcgct ctgtgtccgt tgaa                                            24

<210> SEQ ID NO 16
<211> LENGTH: 24
<212> TYPE: DNA
<213> ORGANISM: Plasmid vector

<400> SEQUENCE: 16
ttcaacggac acagagcgag gacc                                            24

<210> SEQ ID NO 17
<211> LENGTH: 23
<212> TYPE: DNA
<213> ORGANISM: Plasmid vector

<400> SEQUENCE: 17
tttgcgtgtc ctgtgtcgtc gaa                                             23
```

```
<210> SEQ ID NO 18
<211> LENGTH: 23
<212> TYPE: DNA
<213> ORGANISM: Plasmid vector

<400> SEQUENCE: 18
ttcgacgaca caggacacgc aaa                                        23

<210> SEQ ID NO 19
<211> LENGTH: 25
<212> TYPE: DNA
<213> ORGANISM: Plasmid vector

<400> SEQUENCE: 19
atgaccgctc aggaaacctg ttgca                                      25

<210> SEQ ID NO 20
<211> LENGTH: 25
<212> TYPE: DNA
<213> ORGANISM: Plasmid vector

<400> SEQUENCE: 20
ataggcatag taggccagct tgagg                                      25

<210> SEQ ID NO 21
<211> LENGTH: 51
<212> TYPE: DNA
<213> ORGANISM: Plasmid vector

<400> SEQUENCE: 21
tgtgctcctc tttggcttgc ttccaattaa ccctcactaa agggaacgaa t          51

<210> SEQ ID NO 22
<211> LENGTH: 50
<212> TYPE: DNA
<213> ORGANISM: Plasmid vector

<400> SEQUENCE: 22
ctggttcttg tctggcttgg cccaatgcaa caggtttcct gagcggtcat            50

<210> SEQ ID NO 23
<211> LENGTH: 49
<212> TYPE: DNA
<213> ORGANISM: Plasmid vector

<400> SEQUENCE: 23
ggtcctcgct ctgtgtccgt tgaacctcaa gctggcctac tatgcctat             49

<210> SEQ ID NO 24
<211> LENGTH: 49
<212> TYPE: DNA
<213> ORGANISM: Plasmid vector

<400> SEQUENCE: 24
tttgcgtgtc ctgtgtcgtc gaacgactaa tacgactcac tataggcg              49

<210> SEQ ID NO 25
<211> LENGTH: 25
<212> TYPE: DNA
<213> ORGANISM: Plasmid vector

<400> SEQUENCE: 25
gccaatggac tcttagtttt ggaac                                      25
```

```
<210> SEQ ID NO 26
<211> LENGTH: 25
<212> TYPE: DNA
<213> ORGANISM: Plasmid vector

<400> SEQUENCE: 26
gttctggcaa acaaattcgg cgcac                                          25

<210> SEQ ID NO 27
<211> LENGTH: 51
<212> TYPE: DNA
<213> ORGANISM: Plasmid vector

<400> SEQUENCE: 27
tgtgctcctc tttggcttgc ttccaattaa ccctcactaa agggaacgaa t              51

<210> SEQ ID NO 28
<211> LENGTH: 50
<212> TYPE: DNA
<213> ORGANISM: Plasmid vector

<400> SEQUENCE: 28
ctggttcttg tctggcttgg cccaagttcc aaaactaaga gtccattggc                50

<210> SEQ ID NO 29
<211> LENGTH: 49
<212> TYPE: DNA
<213> ORGANISM: Plasmid vector

<400> SEQUENCE: 29
ggtcctcgct ctgtgtccgt tgaagtgcgc cgaatttgtt tgccagaac                 49

<210> SEQ ID NO 30
<211> LENGTH: 25
<212> TYPE: DNA
<213> ORGANISM: Plasmid vector

<400> SEQUENCE: 30
gaaccttggt gtgccaagtt acttc                                          25

<210> SEQ ID NO 31
<211> LENGTH: 25
<212> TYPE: DNA
<213> ORGANISM: Plasmid vector

<400> SEQUENCE: 31
gaactttggc tgaaccccttt gttct                                         25

<210> SEQ ID NO 32
<211> LENGTH: 52
<212> TYPE: DNA
<213> ORGANISM: Plasmid vector

<400> SEQUENCE: 32
tgtgctcctc tttggcttgc gttgaacgac taatacgact cactataggg cg            52

<210> SEQ ID NO 33
<211> LENGTH: 50
<212> TYPE: DNA
<213> ORGANISM: Plasmid vector

<400> SEQUENCE: 33
ctggttcttg tctggcttgg cccaagaagt aacttggcac accaaggttc                50
```

<210> SEQ ID NO 34
<211> LENGTH: 48
<212> TYPE: DNA
<213> ORGANISM: Plasmid vector

<400> SEQUENCE: 34
ggtcctcgct ctgtgtccgt tgaagaacaa ggggttcagc caaagttc           48

<210> SEQ ID NO 35
<211> LENGTH: 48
<212> TYPE: DNA
<213> ORGANISM: Plasmid vector

<400> SEQUENCE: 35
tttgcgtgtc ctgtgtcgtc gaattaaccc tcactaaagg aacgaat            48

<210> SEQ ID NO 36
<211> LENGTH: 25
<212> TYPE: DNA
<213> ORGANISM: Plasmid vector

<400> SEQUENCE: 36
atgccggatc tcctactact gggcc                                    25

<210> SEQ ID NO 37
<211> LENGTH: 25
<212> TYPE: DNA
<213> ORGANISM: Plasmid vector

<400> SEQUENCE: 37
tgtcatagta gacagcgatg gaacg                                    25

<210> SEQ ID NO 38
<211> LENGTH: 53
<212> TYPE: DNA
<213> ORGANISM: Plasmid vector

<400> SEQUENCE: 38
gacaagaacc agttgacgtc aagcttcccg ggacgcgtgc tagcggcgcg ccg      53

<210> SEQ ID NO 39
<211> LENGTH: 50
<212> TYPE: DNA
<213> ORGANISM: Plasmid vector

<400> SEQUENCE: 39
ctggttcttg tctggcttgg cccaaggccc agtagtagga gatccggcat          50

<210> SEQ ID NO 40
<211> LENGTH: 49
<212> TYPE: DNA
<213> ORGANISM: Plasmid vector

<400> SEQUENCE: 40
ggtcctcgct ctgtgtccgt tgaacgttcc atcgctgtct actatgaca           49

<210> SEQ ID NO 41
<211> LENGTH: 50
<212> TYPE: DNA
<213> ORGANISM: Plasmid vector

<400> SEQUENCE: 41

-continued

```
ctggttcttg tctggcttgg cccaaaaagc cgacagccac gctcacaagc          50

<210> SEQ ID NO 42
<211> LENGTH: 49
<212> TYPE: DNA
<213> ORGANISM: Plasmid vector

<400> SEQUENCE: 42
ggtcctcgct ctgtgtccgt tgaagcccaa tgccacagag acagaatgt           49

<210> SEQ ID NO 43
<211> LENGTH: 51
<212> TYPE: DNA
<213> ORGANISM: Plasmid vector

<400> SEQUENCE: 43
ctggttcttg tctggcttgg cccaagttgg atcctctcca aggccccatc t        51

<210> SEQ ID NO 44
<211> LENGTH: 50
<212> TYPE: DNA
<213> ORGANISM: Plasmid vector

<400> SEQUENCE: 44
ggtcctcgct ctgtgtccgt tgaactccag tgccgagtgt gtggggacag          50
```

METHODS OF CREATING CONSTRUCTS USEFUL FOR INTRODUCING SEQUENCES INTO EMBRYONIC STEM CELLS

CROSS REFERENCE TO RELATED APPLICATION

This application is a continuation application of U.S. application Ser. No. 09/193,834, filed Nov. 17, 1998 and now abandoned, which claims benefit of U.S. Provisional Application No. 60/084,949, filed May 11, 1998, and of U.S. Provisional Application No. 60/084,194, filed Nov. 17, 1997.

TECHNICAL FIELD

This invention is in the field of molecular biology and medicine. More specifically, it relates to novel vector constructs and to methods of making DNA constructs for introducing targeted mutations into embryonic stem cells.

BACKGROUND

A major challenge facing biologists today is determining the function of over half a million partial cDNA sequences of various genes, known as expressed sequence tags (ESTs), that are publicly available. In most cases the function of the full-length genes represented by the ESTs remains unknown. Thus, the ability to determine function of these gene sequences is important for disease diagnosis, prediction, prevention and treatment.

In recent years, mouse geneticists have succeeded in creating transgenic animals by manipulating the genes of developing embryos and introducing foreign genes into these embryos. Once these genes have integrated into the genome of the recipient embryo, the resulting embryos or adult animals can be analyzed to determine the function of the gene.

U.S. Pat. Nos. 5,464,764 and 5,487,992 describe one type of transgenic animal in which the gene of interest is deleted or mutated sufficiently to disrupt its function. These "knock-out" animals are made by taking advantage of the phenomena of homologous recombination. (See, also U.S. Pat. Nos. 5,631,153 and 5,627,059). Briefly, conventional targeting DNA vectors contain (1) two blocks of DNA sequences that are homologous to separate regions of the target site; (2) a DNA sequence that codes for resistance to the compound G418 (Neo$^r$) between the two blocks of homologous DNA (i.e. positive selection marker) and (3) DNA sequences coding for herpes simplex virus thymidine kinases (HSV-tk1 and HSV-tk2) outside of the homologous blocks (i.e. negative selection marker). When this vector is introduced into the embryonic stem cell, homologous recombination inserts the Neo$^r$ gene into the target genome, disrupting function of that gene.

The production of constructs useful in producing knock-out animals is a time and labor intensive process. (See, e.g., U.S. Pat. No. 5,464,764) First, genomic clones must be isolated by screening a genomic library with a radioactive probe. To isolate an individual clone requires multiple screens and can take more than 3 weeks. Once the clone is isolated, a restriction map is created in order to aid in the identification of fragments flanking the gene of interest. Again, this process can take several weeks. Finally, the flanking sequences are cloned into the targeting vector. Even in methods which make use of polymerase chain reaction techniques, a partial restriction map of the gene locus is created. (See, Randolph et al. (1996) *Transgenic Research* 5:413–420). In all, using conventional techniques, production of a DNA targeting construct can take several months.

SUMMARY OF THE INVENTION

The present invention provides novel constructs (e.g., plasmid vectors) useful in a rapid and efficient method for generating DNA constructs suitable for introduction into embryonic stem cells. The novel methods described herein eliminate the need for the traditional hybridization isolation of a single genomic clone, restriction mapping of the clone and multiple cloning steps. Thus, the present invention provides an unexpected reduction in the time required for making a "knock-out" vector. Methods described in the art require 2 to 4 months to accomplish what the claimed invention can achieve within 1–2 weeks.

The unexpected increase in efficiency accomplished by the methods described herein involves methods that have not previously been applied to the process of making a "knock-out" vector, including identification of a complex mixture containing the clone of interest, long-range polymerase chain reaction (PCR) and ligation independent cloning. The present inventors are the first to generate a construct without isolating an individual genomic clone or mapping the restriction sites within the clone. Furthermore, the inventors are also the first to generate knock-out constructs using ligation independent cloning, including four-way annealing of nucleotide fragments. The subject invention provides novel constructs and efficient methods of making constructs which, when introduced into embryonic stem cells, deletes or mutates a specific gene in the target animal.

In one aspect, the invention includes a nucleotide construct comprising a sequence encoding a positive selection marker flanked by restriction enzyme sites. The restriction enzyme sites are flanked, on the side opposite the positive selection marker, by sequences which are not complementary to each other and which do not include one of the four types of base pairs at any position. The vector construct can be treated so that single-stranded regions are created at each sequence flanking one side of the restriction enzyme sites. More specifically, the nucleotide construct comprises a sequence encoding a positive selection marker flanked on each side by at least one restriction enzyme site. Preferably, the restriction enzyme site on each side of the positive selection marker is a unique site. Each of the aforementioned restriction enzyme site is flanked by a pair of annealing sites which do not contain at least one type of base at any position. The construct can be treated to create single-stranded regions and this creates the pair of annealing sites. None of the four annealing sites are complementary to each other so that when single-stranded regions are created, they cannot anneal to each other to reseal the vector, i.e., the single stranded regions are incompatible overhangs. However, the single stranded overhangs are compatible with, and can anneal to, the single stranded ends of insert fragments containing sequences homologous to the target gene or a target sequence. The restriction enzyme sites and annealing sites are designed for directional cloning.

Such a construct is illustrated, for example, in FIG. 2A which shows the plasmid pDG2. Plasmid pDG2 contains a unique restriction site, Sac II, between annealing sites 1 and 2 flanking one side of the positive selection marker (Neo$^r$ in this case), and another unique restriction site, Sac I lying between annealing site 3 and site 4 flanking the other side of the positive selection marker.

In one embodiment, single-stranded regions are created by treating the vector with the appropriate restriction enzymes and with a DNA polymerase, for instance, T4 DNA polymerase. This procedure is described in detail in Example 1 below. In one embodiment, the construct comprises a plasmid vector and the positive selection marker is a neomycin resistance gene (Neo$^r$). Preferably, the screening marker on the side of the restriction enzyme sites outside the regions of the construct which are homologous to the target sequence, shown for example in FIG. 7, as opposite the positive selection marker. The screening marker can be green fluorescent protein (GFP) or a modified fluorescent protein.

In another embodiment, the construct of the present invention also includes a negative selection marker on the side of the restriction sites opposite the positive selection marker (e.g., next to the plasmid backbone sequences). The negative selection marker can be thymidine kinase (tk). However, unlike conventional targeted DNA constructs, the constructs described herein do not require, and are preferably made without, a negative selection marker.

In yet another preferred embodiment, the construct is the plasmid vector "pDG2" and has the sequence shown in SEQ ID NO:1. The construct can also be the plasmid vector "pDG4," as shown in SEQ ID NO:2.

In another aspect, the invention provides a method of making a DNA construct usefull in introducing a nucleotide sequence into a target DNA, comprising (a) amplifying a polynucleotide comprising two different nucleotide sequences substantially homologous to the target DNA; and (b) inserting a gene encoding for a positive selection marker between the two different nucleotide sequences substantially homologous to the target DNA. The positive selection marker may be, for example, a neomycin resistance gene (Neo$^r$). Preferably, the amplification step is performed in one-step from a genomic DNA library using, for example, oligonucleotide primers in a PCR reaction. In a preferred embodiment, the library is a plasmid library. In another embodiment, the amplified polynucleotide further comprises a gene encoding a selectable marker, for example, a gene encoding for ampicillin resistance. The vector can also include a second sequence coding for a screening marker, for example, green fluorescent protein (GFP), or another modified fluorescent protein.

In another aspect, the present invention also includes a method of making a DNA construct useful in introducing a nucleotide sequence into a target DNA, comprising: (a) providing a polynucleotide(s) substantially homologous to the target DNA; (b) generating two different fragments of the polynucleotide(s); (c) providing a vector having a gene encoding for a positive selection marker; and (d) using ligation independent cloning to insert the two different fragments into the vector to form the construct, wherein the positive selection marker is between the two different sequence fragments in the construct. The positive selection marker can be a neomycin resistance gene (Neo$^r$) and the vector may be pDG2 (SEQ ID NO:1) or pDG4 (SEQ ID NO:2). The vector can also include a second sequence coding for a screening marker, for example, green fluorescent protein (GFP) or another modified fluorescent protein. The vector can also include a second sequence coding for a negative selection marker.

In another embodiment, the method includes PCR amplifying the fragments with oligonucleotide primers having 5' sequences which do not have one of the four base pairs at any position (also referred to herein as lacking one nucleotide). The 5' sequences lacking one type of base are at least 5, preferably 12, even more preferably at least 20 to 25 nucleotides in length. In one embodiment, the oligonucleotide sequences are shown in SEQ ID NOs 3 to 10. In another embodiment, the oligonucleotide sequences are shown in SEQ ID NOs 3 to 44. The present invention also includes a method of making a DNA construct wherein the ligation independent cloning is performed in one step or in two steps.

The invention also provides a method of disrupting the function of a target sequence or gene in a cell by (a) inserting sequences homologous to the target gene into a construct of the invention as described above, such that the sequences homologous to the target gene flank the positive selection marker, to produce a targeting construct; and (b) introducing the targeting construct into the cell to produce a homologous recombinant wherein the function of the target gene or sequence is disrupted. In a preferred embodiment, the cell is an ES cell. A targeting construct produced by this method is also provided.

Another aspect of the invention is a method of enriching for the desired non-random integrant of the targeting vector wherein homologous recombination between the targeting vector and the target sequence or gene has mutated or disrupted the target gene. The enrichment step involves screening cells that have taken up the targeting construct, with ultraviolet light and identifying cells that do not fluoresce, for further testing by PCR or other methods to confirm the targeted mutation.

In yet another aspect, the invention includes a host cell or an animal containing a construct described herein. Where the construct is a targeting construct, preferably, the targeting construct disrupts the function of the target gene within the host cell or animal.

As will become apparent, preferred features and characteristics of one aspect of the invention are applicable to any other aspect of the invention.

BRIEF DESCRIPTION OF THE DRAWINGS

FIG. 4 (SEQ ID NO:3 through SEQ ID NO:10) shows the nucleic acid sequence before and after T4 polymerase treatment of annealing sites 1–4 contained on the ends of PCR amplified genomic DNA.

FIG. 5 (SEQ ID NO:11 through SEQ ID NO:18) shows the nucleic acid sequence before and after T4 polymerase treatment of annealing sites 1–4 contained within the pDG2 vector.

FIG. 8 shows the sequences of the oligonucleotide primers (SEQ ID NO:19 through SEQ ID NO:44) used in Examples 4 to 10. The lower case sequences are to cloning sites (e.g. ligation independent cloning sequences).

MODES FOR CARRYING OUT THE INVENTION

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

Figure 1:
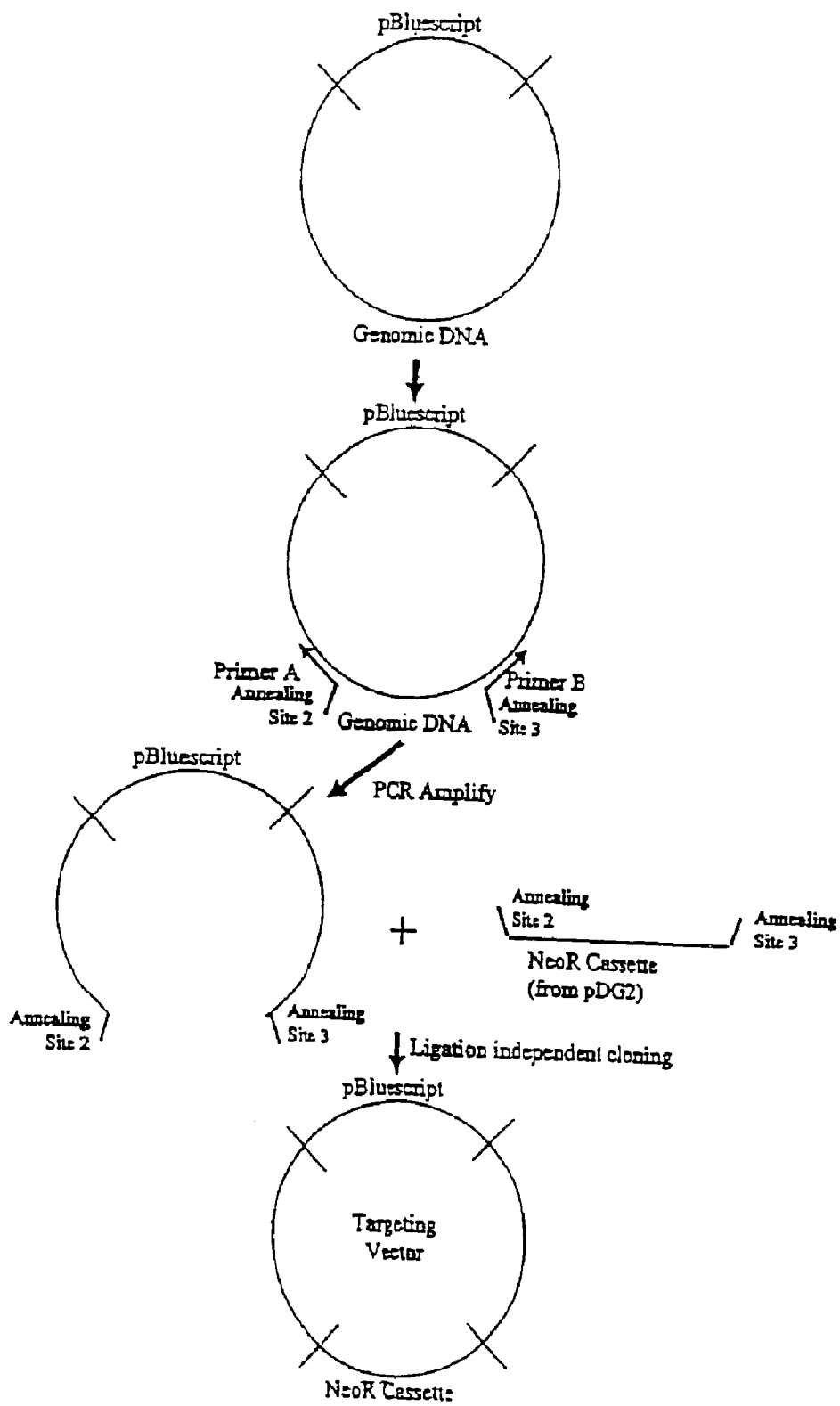
FIG. 1 is a schematic depicting one method of constructing a targeting vector of the present invention. The plasmid PCR method is described in Examples 9 and 10.

In one aspect, the present invention provides a novel fast and efficient method of making a construct suitable for introducing targeted mutations into embryonic stem (ES) cells. In a preferred embodiment, the construct is generated in two steps by (1) amplifing (for example, using long-range PCR) sequences homologous to the target sequence, and (2) inserting another polynucleotide (for example a selectable marker) into the PCR product so that it is flanked by the homologous sequences. Typically, the vector is a plasmid from a plasmid genomic library. The completed construct is also typically a circular plasmid. Thus, as shown in FIG. 1, using long-range PCR with "outwardly pointing" oligonucleotides results in a vector into which a selectable marker can easily be inserted, preferably by ligation independent cloning. The construct can then be introduced into ES cells, where it can disrupt the function of the homologous target sequence.

In another aspect, two separate fragments of a clone of interest are amplified and inserted into a vector containing a positive selection marker using ligation independent cloning techniques. In this embodiment, the clone of interest is generally from a phage library and is identified and isolated using PCR techniques. The ligation independent cloning can be performed in two steps or in a single step.

The methods of the present invention typically result in a finished construct within one week and is thus much more rapid than the several months currently needed to make a knock-out construct using conventional techniques.

The practice of the present invention will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR2: A PRACTICAL APPROACH (M. J. McPherson, B. D. Hames and G. R. Taylor eds., 1995) and ANIMAL CELL CULTURE (R. I. Freshney. Ed., 1987).

Definitions

As used herein, certain terms will have the following specific meanings.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules.

"Oligonucleotide" refers to polynucleotides of between about 5 and about 100 nucleotides of single- or double-stranded DNA. Oligonucleotides are also known as oligomers or oligos and may be isolated from genes, or chemically synthesized by methods known in the art. A "primer" refers to an oligonucleotide, usually single-stranded, that provides a 3'-hydroxyl end for the initiation of enzyme-mediated nucleic acid synthesis.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinycytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentylnyluracil and 2,6-diaminopurine. The use of uracil as a substitute for thymine in a deoxyribonucleic acid is also considered an analogous form of pyrimidine.

A "fragment" (also called a "region") of a polynucleotide is a polynucleotide comprised of at least 9 contiguous nucleotides, preferably at least 15 contiguous nucleotides and more preferably at least 45 nucleotides, of coding or non-coding sequences.

As used herein, "base pair," also designated "bp," refers to the complementary nucleic acid molecules. In DNA there are four "types" of bases: purine adenine (A) is hydrogen bonded with the pyrimidine base thyrnine (T), and the purine guanine (G) with pyrimidine cytosine (C). Each hydrogen bonded base pair set is also known as Watson-Crick base-pairing. A thousand base pairs is often called a kilobase pair, or kb. A "base pair mismatch" refers to a location in a nucleic acid molecule in which the bases are not complementary Watson-Crick pairs. The phrase "does not include at least one type of base at any position" refers to a nucleotide sequence which does not have one of the four bases at any position. For example, a sequence lacking one nucleotide (i.e., lacking one type of base) could be made up of A, G, T base pairs and contain no C residues.

The term "construct" refers to an artificially assembled DNA segment to be transferred into a target tissue, cell line or animal, including human. Typically, the construct will include the gene or a sequence of particular interest, a marker gene and appropriate control sequences. The term "plasmid" refers to an autonomous, self-replicating extra-chromosomal DNA molecule. In a preferred embodiment, the plasmid construct of the present invention contains a positive selection marker positioned between two flanking regions of the gene of interest. Optionally, the construct can also contain a screening marker, for example green fluorescent protein (GFP). If present, the screening marker is positioned outside of and some distance away from the flanking regions.

The term "polymerase chain reaction" or "PCR" refers to a method for amplifying a DNA base sequence using a heat-stable polymerase such as Taq polymerase, and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce exponential and highly specific amplification of the desired sequence. PCR also can be used to detect the existence of the defined sequence in a DNA sample. "Long-range" refers to PCR conditions which allow amplification of large nucleotides stretches, for example, greater than 1 kb.

As used herein, the term "positive selection marker" refers to a gene encoding a product that enables only the cells that carry the gene to survive and/or grow under certain conditions. For example, plant and animal cells that express the introduced neomycin resistance (Neo$^r$) gene are resistant to the compound G418. Cells that do not carry the Neo$^r$ gene marker are killed by G418. Other positive selection markers will be known to those of skill in the art.

"Positive-negative selection" refers to the process of selecting cells that carry a DNA insert integrated at a specific targeted location (positive selection) and also selecting against cells that carry a DNA insert integrated at a non-targeted chromosomal site (negative selection). Non-limiting examples of negative selection inserts include the gene encoding thymidine kinase (tk). Genes suitable for positive-negative selection are known in the art, see e.g., U.S. Pat. No. 5,464,764.

"Screening marker" or "reporter gene" refers to a gene that encodes a product that can readily be assayed. For example, reporter genes can be used to determine whether a particular DNA construct has been successfully introduced into a cell, organ or tissue. Non-limiting examples of screening markers include genes encoding for green fluorescent protein (GFP) or genes encoding for a modified fluorescent protein. "Negative screening marker" is not to be construed as negative selection marker; a negative selection marker typically kills cells that express it.

The term "vector" refers to a DNA molecule that can carry inserted DNA and be perpetuated in a host cell. Vectors are also known as cloning vectors, cloning vehicles or vehicles. The term includes vectors that function primarily for insertion of a nucleic acid molecule into a cell, replication vectors that function primarily for the replication of nucleic acid, and expression vectors that function for transcription and/or translation of the DNA or RNA. Also included are vectors that provide more than one of the above functions. In a preferred embodiment, the vector contains sites useful in the methods described herein contains for example, the vectors "pDG2" or "pDG4" as described herein.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in total DNA complement) to the original parent due to natural, accidental, or deliberate mutation. A host cell includes cells transfected with the constructs of the present invention.

The term "genomic library" refers to a collection of clones made from a set of randomly generated overlapping DNA fragments representing the entire genome of an organism. A "cDNA library" (complementary DNA library) is a collection of all of the mRNA molecules present in a cell or organism, all turned into cDNA molecules with the enzyme reverse transcriptase, then inserted into vectors (other DNA molecules which can continue to replicate after addition of foreign DNA). Exemplary vectors for libraries include bacteriophage (also known as "phage"), which are viruses that infect bacteria, for example lambda phage. The library can then be probed for the specific cDNA (and thus mRNA) of interest. In one embodiment, library systems which combine the high efficiency of a phage vector system with a plasmid system (for example, ZAP system from Stratagene, La Jolla, Calif.) are used in the practice of the present invention.

The term "homologous recombination" refers to the exchange of DNA fragments between two DNA molecules or chromatids at the site of essentially identical nucleotide sequences. Similarly, "substantially homologous" refers to polynucleotide sequences that are essentially identical. For example, homology can be determined using a "blastn" algorithm. It is understood that substantially homologous sequences can accommodate insertions, deletions, and substitutions in the nucleotide sequence. Thus, linear sequences of nucleotides can be essentially identical even if some of the nucleotide residues do not precisely correspond or align.

As used herein the term "ligation independent cloning" is used in the conventional sense to refer to incorporation of a DNA molecule into a vector or chromosome without the use of kinases or ligases. Ligation independent cloning techniques are described, for instance, in Aslanidis and de Jong, (1991) Nucleic Acids Research 18:6069–6074.

A "transgenic animal" refers to a genetically engineered animal or offspring of genetically engineered animals. The transgenic animal usually contains genetic material from at least one unrelated organism, such as from a bacteria, virus, plant, or other animal.

As used herein, the term "target DNA" refers to the nucleic acid molecule or polynucleotide having a sequence in the general population that is not associated with any disease or discernible phenotype. It is noted that in the general population, wild-type genes may include multiple prevalent versions that contain alterations in sequence relative to each other and yet do not cause a discernible pathological effect. These variations are designated "polymorphisms" or "allelic variations."

In a preferred embodiment, the target DNA comprises a portion of a particular gene or genetic locus in the individual's genomic DNA. Preferably, the target DNA comprises part of a particular gene or genetic locus in which the function of the gene product is not known, for example a gene identified using a partial cDNA sequence such as an EST.

The term "exonuclease" refers to an enzyme that cleaves nucleotides sequentially from the free ends of a linear nucleic acid substrate. Exonucleases can be specific for double or single stranded nucleotides and/or directionally specific, for instance, 3'-5' and/or 5'-3'. Some exonucleases exhibit other enzymatic activities, for example, T4 DNA polymerase is both a polymerase and an active 3'-5' exonuclease. Other exemplary exonucleases include exonuclease III which removes nucleotides one at a time from the 5'-end of duplex DNA which does not have a phosphorylated 3'-end, exonuclease VI which makes oligonucleotides by cleaving nucleotides off of both ends of single-stranded DNA, and exonuclease lambda which removes nucleotides from the 5' end of duplex DNA which have 5'-phosphate groups attached to them.

Constructs

The present invention provides novel constructs having multiple sites where 5'-3' single-stranded regions can be created. These constructs, preferably plasmids, include a vector capable of directional, four-way ligation independent cloning. By making use of these novel constructs, the present invention also offers an alternative, time-saving method for preparing a DNA construct. Examples of these constructs are shown in FIGS. 2 and 3.

The constructs typically include a sequence encoding a positive selection marker such as a gene encoding neomycin resistance; a restriction enzyme site on either side of the positive selection marker and a sequence flanking the restriction enzyme sites which does not contain one of the four base pairs. This configuration allows single-stranded ends to be created in the sequence by digesting the construct with the appropriate restriction enzyme and treating the fragments with a compound having exonuclease activity, for example T4 DNA polymerase.

Methods

In one preferred embodiment, a construct suitable for introducing targeted mutations into ES cells is prepared directly from a plasmid genomic library. Using long-range PCR with specific primers, a sequence of interest is identified and isolated from the plasmid library in a single step. Following isolation of this sequence, a second polynucleotide that will disrupt the target sequence can be readily inserted between two regions encoding the sequence of interest. Using this direct method a targeted construct can be created in as little as 72 hours. In another embodiment, a targeted construct is prepared after identification of a clone of interest in a phage genomic library as described in detail below.

The methods described herein obviate the need for hybridization isolation, restriction mapping and multiple cloning steps. Moreover, the function of any gene can be determined using these methods. For example, a short sequence (e.g., EST) can be used to design oligonucleotide probes. These probes can be used in the direct amplification procedure to create constructs or can be used to screen genomic or cDNA libraries for longer full-length genes. Thus, it is contemplated that any gene can be quickly and efficiently prepared for use in ES cells.

1. Generation of Constructs from Plasmid Libraries

A. Plasmid Genomic Libraries

In a preferred embodiment, constructs are prepared directly from a plasmid genomic library. The library can be produced by any method known in the art. Preferably, DNA from mouse ES cells is isolated and treated with a restriction endonuclease which cleaves the DNA into fragments. The DNA fragments are then inserted into a vector, for example a bacteriophage or phagemid (e.g., Lamda ZAP™, Stratagene, La Jolla, Calif.) systems. When the library is created in the ZAP™ system, the DNA fragments are preferably between about 5 and about 20 kilobases.

Preferably, the organism(s) from which the libraries are made will have no discernible disease or phenotypic effects. Preferably, the library is a mouse library. This DNA may be obtained from any cell source or body fluid. Non-limiting examples of cells sources available in clinical practice include ES cells, liver, kidney, blood cells, buccal cells, cerviovaginal cells, epithelial cells from urine, fetal cells, or any cells present in tissue obtained by biopsy. Body fluids include urine, blood, cerebrospinal fluid (CSF), and tissue exudates at the site of infection or inflammation. DNA extracted from the cells or body fluid using any method known in the art. Preferably, the DNA is extracted by adding 5 mL of lysis buffer (10 mM Tris-HCl pH 7.5), 10 mM EDTA (pH 8.0), 10 mM NaCl, 0.5% SDS and 1 mg/mL Proteinase K) to a confluent 100 mm plate of embryonic stem cells. The cells are then incubated at about 60° C. for several hours or until fully lysed. Genomic DNA is purified from the lysed cells by several rounds of gentle phenol:chloroform extractions followed by an ethanol precipitation. For convenience, the genomic library can be arrayed into pools.

B. Long-Range Polymerase Chain Reaction (PCR)

In a preferred embodiment, a sequence of interest is identified from the plasmid library using oligonucleotide primers and long-range PCR. Typically, the primers are outwardly-pointing primers which are designed based on sequence information obtained from a partial gene sequence, e.g., a cDNA or an EST sequence. As depicted for example in FIG. 1, the product will be a linear fragment that excludes the region which is located between each primer.

PCR conditions found to be suitable are described below in the Examples. It will be understood that optimal PCR conditions can be readily determined by those skilled in the art. (See, e.g., PCR 2: A PRACTICAL APPROACH (1995) eds. M. J. McPherson, B. D. Hames and G. R. Taylor, IRL Press, Oxford, Yu et al. (1996) *Methods Mol. Bio.* 58:335–9; Munroe et al. (1995) *Proc. Nat'l Acad. Sci. USA* 92(6) :2209–13). PCR screening of libraries eliminates many of the problems and time-delay associated with conventional hybridization screening in which the library must be plated, filters made, radioactive probes prepared and hybridization conditions established. PCR screening requires only oligonucleotide primers to sequences (genes) of interest. PCR products can be purified by a variety of methods, including but not limited to, microfiltration, dialysis, gel electrophoresis and the like. It may be desirable to remove the polymerase used in PCR so that no new DNA synthesis can occur. Suitable thermostable DNA polymerases are commercially available, for example, Vent™ DNA Polymerase (New England Biolabs), Deep Vent™ DNA Polymerase (New England Biolabs), HotTub™ DNA Polymerase (Amersham), Thermo Sequenase™ (Amersham), rBst™ DNA Polymerase (Epicenter), Pfu™ DNA Polymerase (Stratagene), Amplitaq Gold™ (Perkin Elmer), and Expand™ (Boehringer-Mannheim).

Construct Assembly: Ligation Independent Cloning

To form the completed construct, a sequence which will disrupt the target sequence is inserted into the PCR amplified product. For example, as described herein, the direct method involves joining the long-range PCR product (i.e. the vector) and one fragment (i.e. a gene encoding a selectable marker). As discussed above, the vector contains two different sequence regions substantially homologous to the target DNA sequence. Preferably, the vector also contains a sequence encoding a selectable marker, such as ampicillin. The vector and fragment are designed so that, when treated to form single stranded ends, they will anneal such that the fragment is positioned between the two different regions of substantial homology to the target gene.

Although any method of cloning is suitable, it is preferred that ligation independent cloning strategies be used to assemble the construct comprising two different homologous regions flanking a selectable marker. Ligation independent cloning (LIC) is a strategy for the directional cloning of polynucleotides without the use of kinases or ligases. (See, e.g., Aslanidis and de Jong (1990) *Nucleic Acids Res.* 18:6069–6074; Rashtchian (1995) *Current Opinion in Biotechnology* 6:30–36). Single-stranded tails are created in LIC vectors, usually by treating the vector (at a digested restriction enzyme site) with T4 DNA polymerase in the presence of only one DNTP. The 3' to 5' exonuclease activity of T4 DNA polymerase removes nucleotides until it encounters a residue corresponding to the single dNTP present in the reaction mix. At this point, the 5' to 3' polymerase activity of the enzyme counteracts the exonuclease activity to prevent further excision. The vector is designed such that the single stranded tails created are non-complementary. For example, in the pDG2 vector, none of the single stranded tails of the four annealing sites are complementary to each other. PCR products are created by building appropriate 5' extensions into oligonucleotide primers. The PCR product is purified to remove dNTPs (and original plasmid if it was used as template) and then treated with T4 DNA polymerase in the presence of the appropriate dNTP to generate the specific vector-compatible overhangs. Cloning occurs by annealing of the compatible tails. Single-stranded tails are created at the ends of the cloning fragments, for example using chemical or enzymatic means. Complementary tails are created on the vector; however, to prevent annealing of the vector without insert, the vector tails are not complementary to each other. The length of the tails is at least about 5 nucleotides, preferably at least about 12 nucleotides, even more preferably at least about 20 nucleotides.

In one embodiment, placing the overlapping vector and fragment(s) in the same reaction is sufficient to anneal them. Alternatively, the complementary sequences are combined, heated and allowed to slowly cool. Preferably the heating step is between about 60° C. and about 100° C., more preferably between about 60° C. and 80° C., and even more preferably between about 60° C. and 70° C. The heated reactions are then allowed to cool. Generally, cooling occurs rather slowly, for instance the reactions are generally at about room temperature after about an hour. The cooling must be sufficiently slow as to allow annealing. The annealed fragment/vector can be used immediately, or stored frozen at −20° C. until use.

Further, annealing can be performed by adjusting the salt and temperature to achieve suitable conditions. Hybridization reactions can be performed in solutions ranging from about 10 mM NaCl to about 600 mM NaCl, at temperatures ranging from about 37° C. to about 65° C. It will be understood that the stringency of the hybridization reaction is determined by both the salt concentration and the temperature. For instance, a hybridization performed in 10 mM salt at 37° C. may be of similar stringency to one performed in 500 mM salt at 65° C. For the present invention, any hybridization conditions may be used that form hybrids between substantially homologous complementary sequences.

As shown in FIG. 1, in one embodiment, a construct is made after using any of these annealing procedures where the vector portion contains the two different regions of substantial homology to the target gene (amplified from the plasmid library using long-range PCR) and the fragment is a gene encoding a selectable marker.

After annealing, the construct is transformed into competent *E. coli* cells, for example DH5-alpha cells by methods known in the art, to amplify the construct. The isolated construct is then ready for introduction into ES cells.

2. Generation of Constructs from Phage Libraries

In another embodiment, a clone of interest is identified in a pooled genomic library using PCR. In one embodiment, the PCR conditions are such that a gene encoding a selectable marker can be inserted directly into the positively identified clone. The marker is positioned between two different sequences having substantial homology to the target DNA.

A. Phage Libraries

Genomic phage libraries can be prepared by any method known in the art and as described in the Examples. Preferably, a mouse embryonic stem cell library is prepared in lambda phage by cleaving genomic DNA into fragments of approximately 20 kilobases in length. The fragments are then inserted into any suitable lambda cloning vector, for example lambda Fix II or lambda Dash II (Stratagene, La Jolla, Calif.)

B. Identification of Positive Clones

In order to quickly and efficiently screen a large number of clones from a library, pools may be created of plated libraries. In a preferred embodiment, a genomic lambda phage library is plated at a density of approximately 1,000 clones (plaques) per plate. Sufficient plates are created to represent the entire genome of the organism several times over. For example, approximately 1 million clones (1000 plates) will yield approximately 8 genome equivalents. The plaques are then collected, for example by overlaying the plate with a buffer solution, incubating the plates and recollecting the buffer. The amount of buffer used will vary according to the plate size, generally one 100 mm diameter plate will be overlayed with approximately 4 mL of buffer and approximately 2 mL will be collected.

It will be understood that the individual plate lysates can be pooled at any time during this procedure and that they can be pooled in any combinations. For ease in later identification of single clones, however, it is preferable to keep each plate lysate separately and then make a pool. For example, each 2 mL lysate can be placed in a 96 well deep well plate. Pools can then be formed by taking an amount, preferably about 100 $\mu$l, from each well and combining them in the well of a new plate. Preferably, 100 $\mu$l of 12 individual plate lysates are combined in one well, forming a 1.2 mL pool representative of 12,000 clones of the library.

Each pool is then PCR amplified using a set of PCR primers known to amplify the target gene. The target gene can be a known full-length gene or, more preferably, a partial cDNA sequence obtained from publicly available nucleic acid sequence databases such as GenBank or EMBL. These databases include partial cDNA sequences known as expressed sequence tags (ESTs). The oligonucleotide PCR primers can be isolated from any organism by any method known in the art or, preferably, synthesized by chemical means.

C. Generation of Homologous Fragments

Once a positive clone of the target gene has been identified in a genomic library, two fragments encoding separate portions of the target gene must be generated. In other words, the flanking regions of the small known region of the target (e.g., EST) are generated. Although the size of each flanking region is not critical and can range from as few as 100 base pairs to as many as 100 kb, preferably each flanking fragment is greater than about 1 kb in length, more preferably between about 1 and about 10 kb, and even more preferably between about 1 and about 5 kb. One of skill in the art will recognize that although larger fragments may increase the number of homologous recombination events in ES cells, larger fragments will also be more difficult to clone.

In one embodiment, one of the oligonucleotide PCR primers used to amplify a flanking fragment is specific for library cloning vector, for example lambda phage. Therefore, if the library is a lambda phage library, primers specific for the lambda phage arms can be used in conjunction with primers specific for the positive clone to generate long flanking fragments. Multiple PCR reactions can be set up to test different combinations of primers. Preferably, the primers used will generate flanking sequences between about 2 and about 6 kb in length.

Preferably, the oligonucleotide primers are designed with 5' sequences complementary to the vector into which the fragments will be cloned. In addition, the primers are also designed so that the flanking fragments will be in the proper 3'-5' orientation with respect to the vector and each other when the construct is assembled.

Thus, using PCR-based methods, for example, positive clones can be identified by visualization of a band on an electrophoretic gel.

Figure 3A:
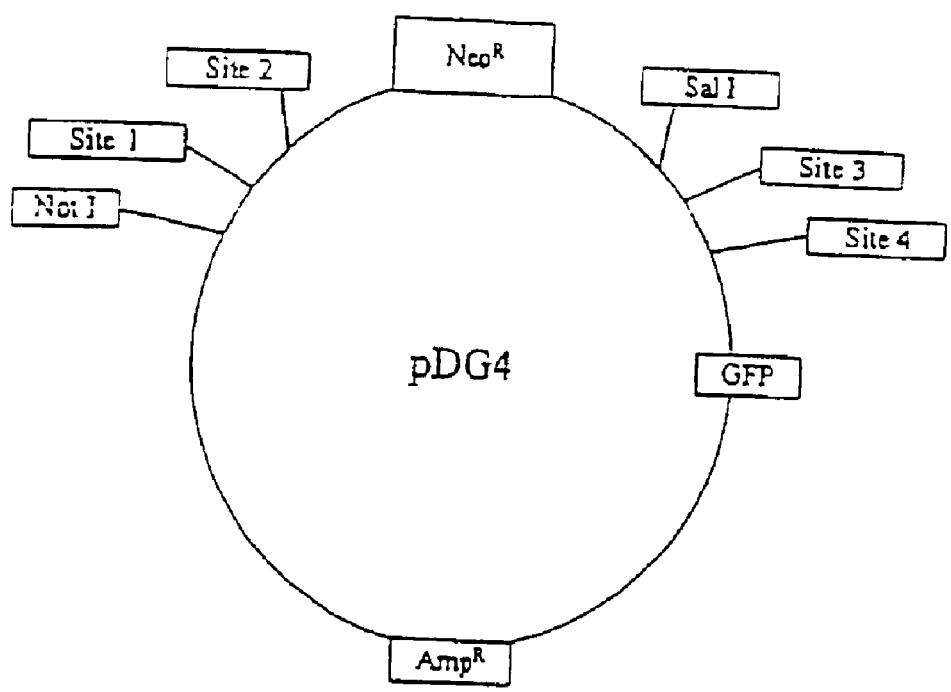
FIG. 3A is schematic depicting the pDG4 vector. The vector contains an ampicillin resistance gene, a neomycin (Neo') gene and a green fluorescent protein (GFP) gene. On each side of the Neo' gene are two sites for ligation independent cloning along with restriction enzyme recognition sites. The sequence of pDG4 is shown in FIGS. 3B1–3B2 and SEQ ID NO:2.
Figure 6:
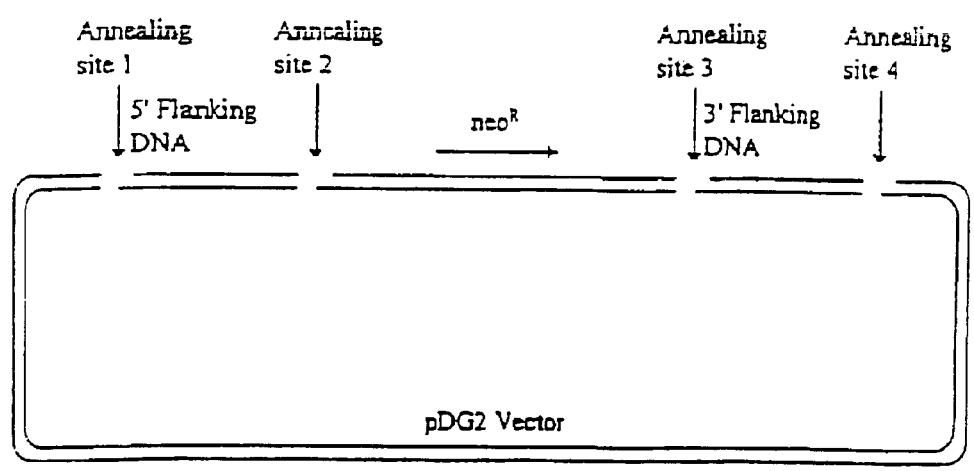
FIG. 6 shows the arrangement of 5' and 3' flanking DNA relative to annealing sites 1, 2, 3 and 4 within the pDG2 vector during an annealing reaction.
Figure 7:
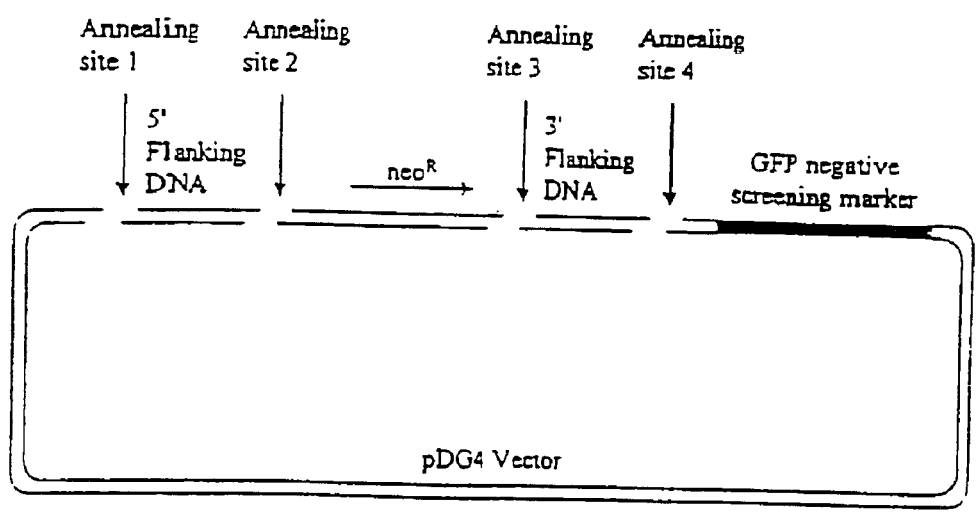
FIG. 7 shows the arrangement of 5' and 3' flanking DNA relative to annealing sties 1, 2, 3 and 4 and the GFP screening marker within the pDG4 vector during an annealing reaction.

In one aspect of the present invention, the cloning involves a vector and two fragments. The vector contains a positive selection marker, preferably Neo$^r$, and cloning sites on each side of the positive selection marker for two different regions of the target gene. Optionally, the vector also contains a sequence coding for a screening marker (reporter gene), preferably, positioned opposite the positive selection marker. The screening marker will be positioned outside the flanking regions of homologous sequences. FIG. 3A shows one embodiment of the vector with the screening marker, GFP, positioned on one side of the vector. However, the screening marker can be positioned anywhere between Not I and Site 4 on the side opposite the positive selection marker, Neo$^R$.

One example of a suitable vector is the plasmid vector shown in FIG. 2 having the sequence of SEQ ID NO:1. The specific nucleic acid ligation independent cloning sites (also referred to herein as annealing sites) labeled "sites 1, 2, 3 or 4" in FIG. 1 are also shown herein. Generally, the cloning sites are lacking at least one type of base, i.e., thymine (T), guanine (G), cytosine (C) or adenine (A). Accordingly, reacting the vector with an enzyme that acts as both a polymerase and exonuclease in presence of only the one missing nucleotide will create an overhang. For example, T4 DNA polymerase acts as both a 3'-5' exonuclease and a polymerase. Thus, when there are insufficient nucleotides available for the polymerase activity, T4 will act as an exonuclease. Specific overhangs can therefore be created by reacting the pDG2 vector with T4 DNA polymerase in the presence of dTTP only. Other enzymes useful in the practice of this invention will be known to those in the art, for instance uracil DNA glycosylase (UDG) (See, e.g., WO 93/18175). The vector exemplified herein has an overhang of 24 nucleotides. It will be known by those skilled in the art that as few as 5 nucleotides are required for successful ligation independent cloning.

In another embodiment, a construct is assembled in a two-step cloning protocol. In the first step, each cloning region of homology is separately cloned into two of the anealing sites of the vector. For example, an "upstream" region of homology is cloned into annealing sites 1 and 2 while in a separate cloning, a "downstream" region of homology is cloned into annealing sites 3 and 4. Once clones containing each single region of homology are identified, a targeting construct containing both regions of homology can be created by digesting each clone with restriction enzymes where one enzyme digests outside of annealing site 1 (e.g., Not I in FIG. 2A) and another enzyme digests between the positive selection marker and annealing site 3 (e.g., Sal I in FIG. 2A). The fragments containing the flanking homology regions from each construct will be purified (e.g. by gel electrophoresis) and combined using standard ligation techniques known in the art, to produce the resulting targeting construct.

In yet another embodiment, a construct according to one aspect of the present invention can be formed in a single-step, four way ligation procedure. The vector and fragments are treated as described above. Briefly, the vector is treated to form two pieces, each piece having a single-stranded tail of specific sequence on each end. Likewise, the PCR amplified flanking fragments are also treated to form single-stranded tails complementary to those of the vector pieces. The treated vector pieces and fragments are combined and allowed to anneal as described above. Because of the specificity of the single-stranded tails, the final construct will contain the fragments separated by the positive selection marker in the proper orientation.

The final plasmid constructs can be used immediately for introduction into ES cells, or stored frozen at −20° C. until use.

The following examples are intended only to illustrate the present invention and should in no way be construed as limiting the subject invention.

EXAMPLES

Example 1

Direct Construct Construction from a Plasmid Library

Genomic libraries using the lambda ZAP™ system were prepared as follows. Embryonic stem cells were grown in 100 mm tissue culture plates. High molecular weight genomic DNA was isolated from these ES cells by adding 5 mL of lysis buffer (10 mM tris-HCL pH 7.5, 10 mM EDTA pH 8.0, 10 mM NaCl, 0.5% SDS, and 1 mg/ml Proteinase K) to a confluent 100 mm plate of embryonic stem cells. The cells were then incubated at 60° C. for several hours or until fully lysed. Genomic DNA was purified from the lysed cells by several rounds of gentle phenol:chloroform extractions followed by ethanol precipitation.

The genomic DNA was partially digested with the restriction enzyme Sau 3A I to generate fragments of approximately 5–20 kb. The ends of these fragments were partially filled in by addition of DATP and dGTP in the presence of Klenow DNA polymerase, creating incompatible ends on the genomic fragments. Size fragments of between 5 and 10 kb were then purified by agarose gel electrophoresis (1× TAE, 0.8% gel). The DNA was then isolated from the excised agarose pieces using a QIAquick gel extraction kit (Qiagen, Inc., Valencia, Calif.).

The genomic fragments were ligated into the Lambda Zap™ II vector (Stratagene, Inc., La Jolla, Calif.) that had been cut with Xho I and partially filled in using dTTP, dCTP, and Klenow DNA polymerase. After ligation, the DNA was packaged using a lambda packaging mix (Gigapack III gold, Stratagene, Inc., La Jolla, Calif.) and the titer was determined.

Circular phagemid DNA was derived from the lambda library by growing the lambda clones on the appropriate bacterial strain (XL-1 Blue MRF', Stratagene, Inc.) in the presence of the M13 helper phage, ExAssist (Stratagene, Inc.). Specifically, approximately 100,000 lambda clones were incubated with a 10–100 fold excess of both bacteria and helper phage for 20 minutes at 37° C. One ml of LB media+10 mM MgSO$_4$ was added to each excision reaction and it was incubated overnight at 37° C. with shaking. Typically 24–96 of these reactions were set up at a time in a 96 well deep-well block. The following morning, the block was heated to 65° C. for 15 minutes to kill both the bacteria and the lambda phage. Bacterial debris was removed by centrifugation at approximately 3000 g for 15 minutes. The supernatant containing the circular phagemid DNA, was retained and used directly in plasmid PCR experiments (see Examples 9 and 10 for plasmid PCR experiments).

The pools of phagemid DNA described above were screened for specific genes of interest using long-range PCR and "outward pointing" oligos, chosen as described above based on the known sequence (depicted in FIG. 1). The PCR reactions contains 2 µl of a pool phagemid DNA sample, 3 µl of 10× PCR Buffer 3 (Boehringer Mannheim), 1.1 µl 10 mM dNTPs, 50 nM primers, 0.3 µl of EXPAND Long Template PCR Enzyme Mix (Boehringer-Mannheim) and 30 µl of $H_2O$. Cycling conditions were 94° C. for 2 minutes (1 cycle); 94° C. for 10 seconds, 65° C. for 30 seconds, 68° C. for 15 seconds (15 cycles); 94° C. for 10 seconds, 60° C. for 30 seconds, 68° C. for 15 seconds plus 20 seconds increase per each additional cycle (25 cycles); 68° C. for 7 minutes (1 cycle) and holding at 4° C.

The products of the PCR reactions were separated by electrophoresis through agarose gels containing 1× TAE buffer and visualized with ethidium bromide and UV light. Any large fragments indicative of successful long-range PCR were excised from the gel and purified using QIAquick PCR purification kit (Qiagen).

In order to eliminate the need to restriction map the PCR fragments, the following ligation independent cloning strategy was employed. The long range PCR fragment of interest was "purified" using a QIAquick PCR purification kit (Qiagen, Inc., Santa Clarita, Calif.). Single-stranded ends of the PCR fragments were generated by mixing: 0.1–2 µg of the fragment; 2 µl of NEB (New England BioLabs) Buffer 4; 1 µl of 2 mM dTTP, 6 units of T4 polymerase (NEB), $H_2O$ to total volume of 20 µl and incubating at 25° C. for 30 minutes. The polymerase is inactivated by heating at 75° C. for 20 minutes. Single-stranded ends were also created on the $Neo^R$ selectable marker fragment by digesting the plasmid vector pDG2 at the unique restriction sites, with SacI and SacII (pDG2 depicted in FIG. 2A) and treating each reaction with T4 polymerase as above. The vector shown in FIG. 1 was prepared with single-stranded ends complementary to those on the long range PCR fragment.

The vector and fragments were then assembled into constructs using either a two-step cloning strategy or a four-way, single-step protocol. Briefly, a reaction containing 10 ng of T4 treated NEO cassette, 2 µl of T4-treated PCR fragment, 0.2 ul of 0.5 M EDTA, 0.3 µl of 0.5 M NaCl and $H_2O$ up to 4 µl was heated to 65° C. and allowed to cool to room temperature over approximately 45 minutes. The mixture was then transformed into subcloning DH5-α efficiency competent cells.

Example 2

Generation of Constructs from Phage Libraries

A mouse embryonic stem cell library was prepared in lambda phage as follows. Genomic libraries were constructed from genomic DNA by partial cleavage of DNA at Sau 3AI sites to yield genomic fragments of approximately 20 kb in length. The terminal sequences of these DNA fragments were partially filled in using Klenow enzyme in the presence of dGTP and DATP and the fragments were ligated using T4 DNA ligase into Xho I sites of an appropriate lambda cloning vector, e.g., lambda Fix II (Stratagene, Inc., La Jolla, Calif.), which had been partially filled in using Klenow in the presence of dTTP and dCTP. Alternatively, the partially digested genomic DNA was size selected using a sucrose gradient and sequences of approximately 20 kb selected for. The enriched fraction was cloned into a Bam HI cut lambda vector, e.g., lambda Dash II (Stratagene, Inc., La Jolla, Calif.).

The library was plated onto 1,152 plates, each plate containing approximately 1,000 clones. Thus, a total of 1.1 million clones (the equivalent of 8 genomes) was plated.

The phage were eluted from each plate by adding 4 mL of lambda elution buffer (10 mM $MgCl_2$, 10 mM Tris-pH 8.0) to each plate and incubating for 3 to 5 hours at room temperature. After incubation, 2 mL of buffer was collected from each plate and placed into one well of a 96 deep well plate (Costar, Inc.). Twelve 96-well plates were filled and referred to as the "sub-pool library."

Using the sub-pool library, "pool libraries" were made by placing 100 µl of 12 different sub-pool wells into one well of a new 96 well plate. The 12 sub-pool plates were combined to form 1 plate of pool libraries.

Using a pair of oligonucleotides that were known to PCR amplify the gene of interest, supernatant from the 96 pools of the "large-pool library" were amplified. PCR was performed in the presence of 0.5 units of Amplitaq Gold™ (Perkin Elmer), 1 µM of each oligonucleotide, 200 µM dNTPs, 2 µl of a 1 to 5 dilution of the pool (or subpool) supernatant, 50 mM KCl, 100 mM Tris-HCl (pH 8.3), and either 1.5 mM or 1.25 mM $MgCl_2$. Cycling conditions were 95° C. for 8 minutes (1 cycle); 95° C. for 30 seconds, 60° C. for 30 seconds, 72° C. for 45 seconds (55 cycles); 72° C. for 7 minutes (1 cycle) and holding at 4° C. Depending on the gene, between about 3 and 12 pools yielded positive signals as identified on agarose gels as described in Example 1. In cases where further purification was necessary (i.e. where a clear signal was not present after amplification), the 12 sub-pools making up the pool were subjected to amplification using the same primers and a single sub-pool (1000 clones) was identified.

Generation of flanking fragments

As described above, knock-out constructs contain two blocks of DNA sequence homologous to the target gene, flanking a positive selection marker. Long range PCR was performed from the pools of lambda clones positively identified as described above in Example 2. Each fragment was generated using a pair of oligonucleotides with predetermined sequences lacking one type of base and complementary to predetermined sequences on the vector. The fragments obtained were between 1 and 5 kb. A third fragment, longer than 5 kb, is also generated using appropriate oligonucleotides. This third fragment was then used to obtain DNA sequences near the gene to be knocked out but outside of the vector.

Example 3

Two-Step Cloning—General Procedure

The pDG2 plasmid vector (FIG. 2A) contains unique restriction sites SacII and Sac I. Appropriate single-stranded annealing sites were generated by digesting the pDG2 vector with either restriction enzyme SacII or SacI and treating each reaction with T4 polymerase and dTTP as described above. Four reactions were set up in microtiter plates for each vector, the reaction containing 1 µl of T4-treated vector, 0.2 µl of 0.5M EDTA, 3 µl of 0.5M NaCl and 0.5 µl $H_2O$ and 1 µl of either (1) T4 polymerase-treated fragments; (2) a 1:10 dilution of the T4-treated fragments reaction; (3) a 1:100 dilution of the T4-treated fragments or (4) $H_2O$ (no insert control). The microtiter plates were sealed, placed in-between two temperature blocks heated to 65° C., and allowed to cool slowly at room temperature for 30 to 45 minutes.

The microtiter plate was then placed on ice and 20–25 μl of subcloning efficiency competent cells added to each well. The plate was incubated on ice for 20-30 minutes. The microtiter plate was then placed between two temperature blocks heated to 42° C. for 2 minutes, followed by 2 minutes on ice. 100 μl of LB was added to each well, the plate covered with parafilm and incubated 30–60 minutes at 37° C. The entire contents of each well were plated on one LB-Amp plate and incubated at 37° C. overnight.

Between about 12–24 colonies were picked from plates which had at least 2–4 times more colonies than the no insert control. The colonies were grown in deep well plates overnight at 37° C. and then the plasmid DNA extracted using a Qiagen mini-prep kit.

Figure 2A:
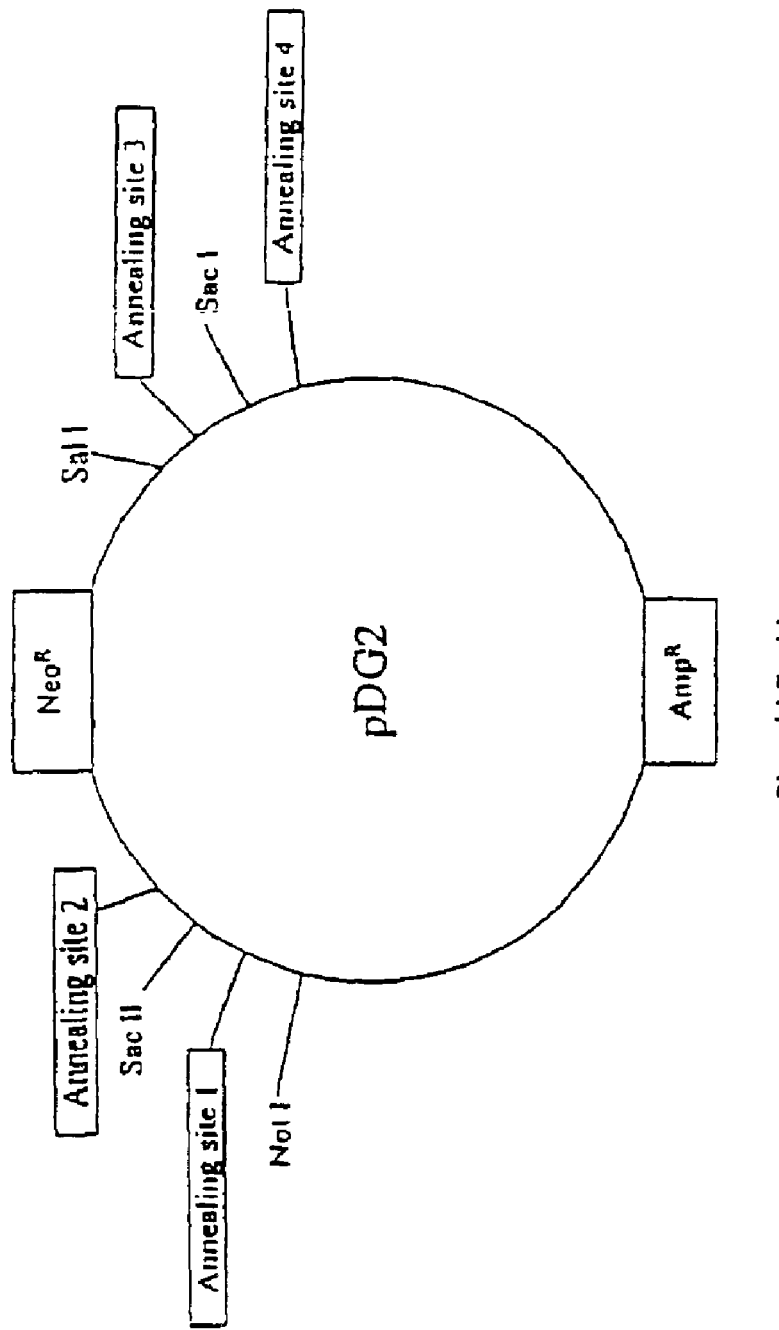
FIG. 2A is a schematic depicting the pDG2 vector. The vector contains an ampicillin resistance gene and a neomycin (Neo$^r$) gene. On each side of the Neo$^r$ gene are two sites for ligation independent cloning along with restriction sites. The sequence of pDG2 is shown in FIG. 2B and SEQ ID NO:1.

The plasmid DNA was digested with Not I and Sal I enzymes. As shown in FIG. 2A, a Not I/Sal I digestion will generate a large fragment containing cloning sites 3 and 4 and a smaller fragment containing cloning sites 1 and 2 and the Neo$^r$ gene. After digestion, the reactions were run on a 0.8% agarose gel containing 0.2 μg/mL ethidium bromide. For no inserts, two bands were present, one of 1975 base pairs and one of 2793 base pairs. When an insert fragment was present, at least one of these bands would be larger because it would also contain a fragment (insert 1 or 2) either at the annealing site ½ or the site ¾. The insert bands were excised and treated with a QIAquick gel extraction kit. A second ligation reaction was performed containing 1 μl of 10× ligase buffer (50 mM Tris-HCl pH 7.5, 10 mM MgCl$_2$, 10 mM dithiothreitol, 1 mM ATP, 25 μg/mL bovine serum albumin), 1 μl T4 DNA ligase, 1–2 μl fragment (site ¾ band), 5 μl of site ½ band and H$_2$O up to 10 μl. Controls were also set up replacing either the site ¾ fragment or the site ½ fragment with water. The reactions were incubated 1 to 2 hours at room temperature and transformed with 25 μl of competent cells.

The following description applies to the Examples that follow. The sequences of the target genes are known and publicly available and were primarily obtained from the EST database. The oligo primers for PCR amplification of the target genes were prepared based on these sequences. "Flanking DNA" in the context of these examples refers to the genomic sequences flanking the region in the target gene that is to be deleted or mutated. "Flanking DNA" is also described above as the blocks of DNA sequence homologous to the target gene. RI genomic library refers to a genomic library prepared from the R1 ES cell line. Such libraries can be prepared such as described in Example 1. To date, the methods of the invention have been practiced in about 200 known and novel target genes.

Example 4

Two-way Cloning of Targeting Construct for Target 2, a Metalloprotease Gene

Identification of flanking DNA for Target 2, a metalloprotease gene

Individual pools of an R1 genomic library were PCR amplified under standard conditions using oligos #174 (SEQ ID NO:19) and #180 (SEQ ID NO:20) in order to identify individual wells containing genomic DNA of target #2 as indicated by the presence of a 500 bp band. A total of 12 pools, each containing approximately 12,000 clones were identified (pools A5, A7, C2, D2, E5, E10, F7, G1, G7, H2, H4, H7). Pool C2 was then amplified using oligos 454 (SEQ ID NO:21) and 463 (SEQ ID NO:22) to generate a 2000 bp band, and pool H2 was amplified using oligos 464 (SEQ ID NO:23) and 42 (SEQ ID NO:24) to generate a 2700 bp band. These two bands contained flanking DNA for target 2.

Construction of targeting construct

Each band containing flanking DNA for target 2 was gel purified from an agarose gel and the ends were treated individually with T4 DNA polymerase in the presence of dTTP in order to produce single stranded overhangs. Each of these bands was then cloned individually into plasmid vector pDG2 (shown in FIG. 2A). The C2 band was cloned into Sac II-digested pDG2 that had been treated with T4 DNA polymerase in the presence of dATP, by ligation independent cloning. In a separate reaction, the H2 band was cloned into Sac I-digested pDG2 that had been treated with T4 DNA polymerase in the presence of dATP by ligation independent cloning.

In order to move the two flanking arms into a single targeting vector, each vector above was digested with Not I/Sal I and the 4 kb fragment containing the C2 band and the 5 kb fragment containing the H2 band were gel purified. These two fragments were ligated together with T4 DNA ligase using standard conditions, and recombinants containing both flanking arms were identified. Out of 12 colonies examined, all 12 were correct, i.e. contained both arms correctly flanking the positive selection marker, Neo$^R$.

Example 5

Two-way Cloning of Targeting Construct for Target 54, a Serine Protease Gene

Identification of flanking DNA for target 54:

Individual pools of an R1 genomic library were PCR amplified under standard conditions using oligos #151 (SEQ ID NO:25) and #155 (SEQ ID NO:26) in order to identify individual wells containing genomic DNA of target #54 as indicated by the presence of a 179 bp band. A total of 12 pools, each containing approximately 12,000 clones were identified (pools A4, A10, B2, B9, C9, E1, E6, F8, G4, H6, H7, and H9). Pool G4 was then amplified using oligos 454 (SEQ ID NO:27) and 465 (SEQ ID NO:28) to generate a 1400 bp band and pool H7 was amplified using oligos 466 (SEQ ID NO:29) and 42 (SEQ ID NO:24) to generate a 3000 bp band. These two bands contained flanking DNA for target 54.

Construction of targeting construct

Each band was gel purified from an agarose gel and the ends were treated individually with T4 DNA polymerase in the presence of dTTP in order to produce single stranded overhangs. Each of these bands were then cloned individually into pDG2. The G4 band was cloned into Sac II cut pDG2 that had been treated with T4 DNA polymerase in the presence of dATP by ligation independent cloning. In a separate reaction, the H7 band was cloned into Sac I cut pDG2 that had been treated with T4 DNA polymerase in the presence of DATP by ligation independent cloning.

In order to move the two flanking arms into a single targeting vector, each vector above was digested with Not I/Sal I and the 6 kb fragment containing the G4 band and the 8 kb fragment containing the H7 band were gel purified. These two fragments were ligated together with T4 DNA ligase using standard conditions and recombinants containing both flanking arms were identified. Out of 24 colonies examined, 14 had the correct inserts.

Example 6

Single-Step (Four-Way) Cloning—General Procedure

Because each single-stranded annealing site is unique, a four-way ligation strategy was also used to generate constructs in a single step. The annealing reactions were set up as described above except that each reaction contained a vector digested with both SacI and SacII, and both T4-treated fragments were added to these reactions.

Example 7

Four-Way Cloning of Targeting Construct for Target 43, a Gene for a G-Protein Coupled Receptor Identification of flanking DNA for target 43:

Individual pools of an R1 genomic library were PCR amplified under standard conditions using oligos #1 (SEQ ID NO:30) and #2 (SEQ ID NO:31) in order to identify individual wells containing genomic DNA of target #43 as indicated by the presence of a 414 bp band. A total of 11 pools, each containing approximately 12,000 clones were identified (pools A3, A5, A9, B4, D4, D10, E1, E9, F9, G7, and G8). Pool E1 was then amplified using oligos 41 (SEQ ID NO:32) and 38 (SEQ ID NO:33) to generate a 1500 bp band and pool D10 was amplified using oligos 40 (SEQ ID NO:34) and 37 (SEQ ID NO:35) to generate a 3500 bp band. These two bands contained flanking DNA for target 43.

Construction of targeting construct

Each band was gel purified from an agarose gel and the ends were treated individually with T4 DNA polymerase in the presence of dTTP in order to produce single stranded overhangs. These inserts were then mixed with ~50 ng of pDG2 that had been digested with both Sac I and Sac II followed by treatment with T4 DNA polymerase in the presence of dATP. The DNA mixture was heated to 65° C. for 2 minutes followed by a 5 minute incubation on ice. The annealed DNA was then transformed into competent DH5α cells and recombinant molecules were obtained by selection on ampicilin agarose plates. After incubation overnight at 37° C., individual colonies were picked and grown up for analysis. Recombinant molecules were identified by appropriate restriction enzyme digestion. Out of 52 colonies examined, 35 had the correct restriction pattern for the expected product.

Example 8

Four-Way Cloning of Targeting Construct for Target 244, a Novel Gene

Identification of flanking DNA for target 244

Individual pools of an R1 genomic library were PCR amplified under standard conditions using oligos #540 (SEQ ID NO:36) and #546 (SEQ ID NO:37) in order to identify individual wells containing genomic DNA of target #244 as indicated by the presence of a 246 bp band. A total of 16 pools, each containing approximately 12,000 clones were identified (pools A1, B1, A3, A5, A6, B6, A8, C9, D10, E1, F2, E5, E6, F10, G9, and H8). Pool G9 was then amplified using oligos 445 (SEQ ID NO:38) and 667 (SEQ ID NO:39) to generate a 1300 bp band and pool A6 was amplified using oligos 668 (SEQ ID NO:40) and 42 (SEQ ID NO:24) to generate a 1600 bp band. These two bands contained flanking DNA for target 244.

Construction of Targeting Construct

Each band was gel purified from an agarose gel and the ends were treated individually with T4 DNA polymerase in the presence of dTTP in order to produce single stranded overhangs. These inserts were then mixed with ~50 ng of pDG2 that had been digested with both Sac I and Sac II followed by treatment with T4 DNA polymerase in the presence of dATP. The DNA mixture was heated to 65° C. for 2 minutes followed by a 5 minute incubation on ice. The annealed DNA was then transformed into competent DH5α cells and recombinant molecules were obtained by selection on ampicilin agarose plates. After incubation overnight at 37° C., individual colonies were picked and grown up for analysis. Recombinant molecules were identified by appropriate restriction enzyme digestion. Out of 12 colonies examined, 2 had the correct restriction pattern for the expected product.

Examples 9 and 10 below provide the plasmid PCR method (schematized in FIG. 1) as an alternative and preferred method over the 2-way and 4-way strategies described in the Examples above.

Example 9

Plasmid PCR Method of Cloning Targeting Construct for Target 227, a Novel Gene Amplification of Genomic Clone Individual pools of a plasmid PCR genomic library made from R1 ES cells, cloned into lambda Zap II and subsequently excised using M13 helper phage mediated-excision, were amplified using oligos 907 (SEQ ID NO:41) and 908 (SEQ ID NO :42). These oligos amplified a product of approximately 9 kb from pool 6 of the library. This fragment, containing both flanking arms for target 227 as well as the plasmid pBluescript backbone, was isolated from an agarose gel.

Construction of Targeting Construct

The isolated DNA fragment was treated with T4 DNA polymerase in the presence of dTTP in order to generate appropriate single-stranded ends. This fragment was then annealed (ligation independent) with a neo gene fragment obtained from pDG2 that had been digested with both Sac I and Sac II followed by treatment with T4 DNA polymerase in the presence of dATP. The digestion and polymerase treatment yielded a neo gene with ends that would specifically anneal to the target 227 fragment. Annealing reactions were set up essentially as described above and a target 227 construct was obtained (13 out of 14 clones were correct).

Example 10

Plasmid PCR Method of Cloning Targeting Construct for Target 125, a Nuclear Hormone Receptor Gene Amplification of Genomic Clone Individual pools of a plasmid PCR library made from R1 ES cells, cloned into lambda Zap II and subsequently excised using M13 helper phage mediated excision were amplified using oligos 1157 (SEQ ID NO:43) and 1158 (SEQ ID NO:44). These oligos amplified a product of approximately 10 kb from pool 10 of the library. This fragment, containing both flanking arms for target 125 as well as a pBluescript backbone, was isolated from an agarose gel.

Construction of Targeting Construct

The isolated DNA fragment was treated with T4 DNA polymerase in the presence of dTTP in order to generate appropriate single-stranded ends. This fragment was then annealed with a neo gene fragment obtained from pDG2 that had been digested with both Sac I and Sac II followed by treatment with T4 DNA polymerase in the presence of DATP. This yielded a neo gene with ends that would specifically anneal to the target 125 fragment. Annealing reactions were set up essentially as described above and a target 125 construct was obtained (12 out of 18 clones were correct).

Example 11

Use of GFP as Screening Marker

The addition of the GFP (Green Fluorescent Protein) gene outside the region of homology with the target gene allows one to enrich for homologous recombinants (recombination occurring between the targeting construct and the target gene in the ES cell) by screening ES cell colonies under a fluorescent light. Rapidly growing ES cells were trypsinized to make single cell suspensions. The respective targeting vector was linearized with a restriction endonuclease and 20 µg of DNA was added to $10 \times 10^6$ ES cells in ES medium {High Glucose DMEM (without L-Glutamine or Sodium Pyruvate) with LIF (Leukemia Inhibitory Factor-Gibco 13275-029 "ESGRO") 1,000 units/ml, and 12% Fetal Calf Serum}. Cells were placed into a 2 mm gap cuvette and electroplated on a BTX electroporator at 400 µF resistance and 200 volts. Immediately after electroporation, ES cells were plated at $1 \times 10^6$ cells per 100 mm gelatinized tissue culture plate. 48 hours later, media was changed to ES media+G418 (200 ug/ml). Media was changed on days 4, 6, and 8 with ES media+G418 (200 ug/ml). On days 10–12 the plates were then placed under an ultraviolet light and the ES cell colonies were scored on whether or not they were fluorescent. The basis of this experiment is that the fluorescent cells have randomly integrated the targeting vector and the GFP gene is intact. Cells that have undergone homologous recombination will have deleted the GFP gene and not fluoresce; these are the clones of interest.

Tables 1 and 2 below show the results of typical GFP screening experiments. These data were from experiments involving 4 different target genes. This GFP screening procedure has been used successfully to enrich for homologous recombinants for 12 different target genes thus far.

Table 1 shows the data for 3 targeted genes where ES colonies were previously tested for homologous recombination without a GFP gene marker; in two cases no homologous integrants were found. For the third gene, only 1 recombinant was found in 907 ES colonies that were tested. The GFP gene was then inserted in the targeting vector outside the region of homology and the experiments were repeated as described above. After selecting only ES colonies that do not express the GFP, homologous recombinants were found for all 3 genes. The enrichment was 4–5 fold, thus decreasing substantially the number of colonies that must be screened. In Table 2, data is presented in which a fourth gene was targeted with a knock-out construct containing a GFP screening marker. In this experiment, an equivalent number of colonies were tested for homologous recombination from colonies that were picked at random compared to those that were screened for GFP loss. There was only a single homologous recombinant in the randomly picked colonies as compared to 4 in those screened for GFP expression. These data indicate that the addition of GFP screening marker to targeting vectors significantly reduces the number of colonies that must be assayed to find homologous recombinants in ES cells.

TABLE 1

KO Rates with GFP prescreening compared to KO rates of previous, non-GFP prescreened electroporations

| Target # | GFP Construct(s) | Total Neor colonies | Total GFP colonies | Theoretical Enrichment | Total KOs in GFP(-) colonies | KO rate in GFP(-) colonies | KO rate for non-GFP constructs |
|---|---|---|---|---|---|---|---|
| 65 | 273 | 750 | 179 | 4.2-fold | 7 | 1/25 | 1/907 |
| 67 | 269, 270 | 2029 | 416 | 4.7-fold | 2 | 1/208 | 0/986 |
| 235 | 275 | 970 | 225 | 4.0-fold | 1 | 1/225 | 0/542 |

TABLE 2

KO Rates of Identical GFP-tagged constructs with and without GFP prescreening

| Target # | GFP Construct(s) | Total Neor colonies | Total GFP colonies | Theoretical Enrichment | Total KOs screened for KO | Total KO's | KO rate |
|---|---|---|---|---|---|---|---|
| 17 | 277, 278 | 1000 | not GFP screened | none | 192 | 1 | 1/192 |
| 17 | 277, 278 | 1002 | 174 | 5.8-fold | 174 | 4 | 4/174 |

Example 12

Production of Mice with Mutated Gene

After the colonies that are non-flourescent have been identified, they are picked into 96-well plates with trypsin. After the colonies have been in the typsin for 5–10 minutes the cells are divided into duplicate plates containing ES medium (one plate to freeze and one plate from which to make DNA to screen the colonies for homologous recombination events). The plate for freezing is typically grown for 2–5 days before it is frozen (freeze media: 50% FBS, 40% DMEM and 10% DMSO). The DNA plate is typically overgrown and refed for 8–10 days before it is lysed to prepare DNA for PCR or Southern blot analysis (lysis buffer: 10 mM TRIS pH 7.5, 10 mM EDTA pH 8.0, 10 mM NaCl, 0.5% sarcosyl and 1 mg/ml Proteinase K). The DNA is then precipitated with 2 volumes of ethanol and resuspended in the appropriate buffer for PCRs or restriction enzyme digestion.

Upon confirmation of homologous recombination events, the positive well(s) is thawed into a 24-well tissue culture dish that has been previously plated with mitomycin C treated mouse embryonic fibroblasts (24 hours prior). The cells are grown up to sufficient levels for diploid aggregation (CD-1 host strain) or blastocyst injection (C57BL/6 host strain) and also for additional freezing of stock vials. For general procedures for the handling of ES cells and the production of chimeric mice from ES cells, refer to Teratocarcinomas and Embryonic Stem Cells-a Practical Approach (Ed. E J Robertson, IRL Press Limited, 1987). The blasto cysts are then implanted in pseudo pregnant female CD-1 mice. Offspring are born 17–20 days later. Highly chimeric mice are then bred to produce germline transmission of the mutated gene.

As is apparent to one of skill in the art, various modification and variations of the above embodiments can be made without departing from the spirit and scope of this invention. These modifications and variations are within the scope of this invention.

What is claimed is:

1. A method of producing a targeting construct, the method comprising:
   (a) amplifying a polynucleotide sequence comprising a first sequence homologous to a first region of a target gene sequence and a second sequence homologous to a second region of said target gene sequence;
   (b) providing a gene encoding a positive selection marker; and
   (c) annealing the gene encoding the positive selection marker with the polynucleotide sequence to form the construct using ligation independent cloning, such that the gene encoding the positive selection marker is positioned between the first homologous sequence and the second homologous sequence;
   wherein the first sequence and second sequence are capable of homologously recombining with the target gene sequence.

2. The method of claim 1, wherein the polynucleotide sequence is amplified directly from a plasmid library.

3. The method of claim 1, wherein the gene encoding the positive selection marker is a neomycin resistance gene.

4. The method of claim 1, wherein the polynucleotide sequence is amplified with oligonucleotide primers each comprising a 5' terminal sequence that comprises at least 5 nucleotides selected from no more than three of the following types of nucleotides: A, T, C and G.

5. The method of claim 1, wherein the construct further comprises a gene encoding screening marker.

6. The method of claim 6, wherein the screening marker is a fluorescent protein.

7. A method of producing a targeting construct, the method comprising:
   (a) providing a circular plasmid library comprising nucleotide fragments corresponding to a target gene sequence;
   (b) amplifying from the circular plasmid library a polynucleotide sequence comprising a first sequence homologous to a first region of said target gene sequence and a second sequence homologous to a second region of said target gene sequence; and
   (c) inserting a gene encoding a positive selection marker between the first sequence and the second sequence to form the construct using ligation independent cloning,
   wherein the first sequence and the second sequence are capable of homologously recombining with the target gene sequence.

8. The method of claim 7, wherein the gene encoding the positive selection marker is a neomycin resistance gene.

9. The method of claim 7, wherein the polynucleotide sequence is amplified with oligonucleotide primers each comprising a 5' terminal sequence that comprises at least 5 nucleotides in length selected from no more than three of the following types of nucleotides: A, T, C and G.

10. The method of claim 7, wherein the construct further comprises a gene encoding a screening marker.

11. The method of claim 10, wherein the screening marker is a fluorescent protein.

12. The method of claim 4, wherein the 5' terminal sequence comprises at least 12 nucleotides selected from no more than three of the following types of nucleotides: A, T, C and G.

13. The method of claim 12, wherein the 5' terminal sequence comprises at least 20 nucleotides selected from no more than three of the following types of nucleotides: A, T, C and G.

14. The method of claim 9, wherein the 5' terminal sequence comprises at least 12 nucleotides selected from no more than three of the following types of nucleotides: A, T, C and G.

15. The method of claim 14, wherein the 5' terminal sequence comprises at least 20 nucleotides selected from no more than three of the following types of nucleotides: A, T, C and G.

* * * * *